(12) United States Patent
Chen et al.

(10) Patent No.: US 11,458,208 B2
(45) Date of Patent: Oct. 4, 2022

(54) DESMOGLEIN 2 ANTIBODY FUSION PROTEINS FOR DRUG DELIVERY

(71) Applicant: ASCLEPIUMM TAIWAN CO., LTD, New Taipei (TW)

(72) Inventors: Min-che Chen, New Taipei (TW); Ya-chuan Liu, New Taipei (TW); Po-hao Chang, New Taipei (TW); Ya-ping Tsai, New Taipei (TW); Chun-wei Chen, New Taipei (TW); Pei-yi Lee, New Taipei (TW)

(73) Assignee: ASCLEPIUMM TAIWAN CO., LTD, New Taipei (TW)

( * ) Notice: Subject to any disclaimer, the term of this patent is extended or adjusted under 35 U.S.C. 154(b) by 658 days.

(21) Appl. No.: 16/307,448

(22) PCT Filed: Jun. 6, 2017

(86) PCT No.: PCT/CN2017/087350
§ 371 (c)(1),
(2) Date: Jun. 6, 2019

(87) PCT Pub. No.: WO2017/211278
PCT Pub. Date: Dec. 14, 2017

(65) Prior Publication Data
US 2019/0298848 A1    Oct. 3, 2019

Related U.S. Application Data

(60) Provisional application No. 62/346,386, filed on Jun. 6, 2016.

(51) Int. Cl.
| A61K 47/68 | (2017.01) |
| C07K 16/30 | (2006.01) |
| A61P 35/00 | (2006.01) |
| A61K 9/00 | (2006.01) |
| C12N 15/87 | (2006.01) |
| A61K 39/00 | (2006.01) |

(52) U.S. Cl.
CPC ........ *A61K 47/6811* (2017.08); *A61K 9/0019* (2013.01); *A61P 35/00* (2018.01); *C07K 16/30* (2013.01); *C12N 15/87* (2013.01); *A61K 2039/505* (2013.01); *C07K 2319/10* (2013.01); *C07K 2319/50* (2013.01); *C07K 2319/55* (2013.01)

(58) Field of Classification Search
None
See application file for complete search history.

(56) References Cited

U.S. PATENT DOCUMENTS

| 6,072,041 A | 6/2000 | Davis et al. |
| 2013/0071395 A1 | 3/2013 | Basilion |
| 2014/0140976 A1 | 5/2014 | Rosenblum et al. |

| 2016/0008480 A1 | 1/2016 | Lee et al. |
| 2016/0151512 A1 | 6/2016 | Kim |
| 2016/0185875 A1 | 6/2016 | Cheng et al. |

FOREIGN PATENT DOCUMENTS

| CN | 102816795 A | 12/2012 |
| CN | 102858367 A | 1/2013 |
| CN | 104822698 A | 8/2015 |
| CN | 105079817 A | 11/2015 |
| CN | 105593242 A | 5/2016 |
| JP | 2007-511209 A | 5/2007 |
| JP | 2011-529079 A | 12/2011 |
| JP | 2014-521661 A | 8/2014 |
| WO | 200107084 A1 | 2/2001 |
| WO | 2006074451 A2 | 7/2006 |
| WO | 2008015841 A1 | 2/2008 |
| WO | 2008121898 A1 | 10/2008 |
| WO | 2009025846 A2 | 2/2009 |
| WO | 2011072124 A1 | 6/2011 |
| WO | 2012113846 A1 | 8/2012 |
| WO | 2012154530 A1 | 11/2012 |
| WO | 2013006706 A1 | 1/2013 |
| WO | 2014055836 A2 | 4/2014 |
| WO | 2014193973 A2 | 12/2014 |
| WO | 2015006744 A1 | 1/2015 |

OTHER PUBLICATIONS

Firer, M.A.et al. "Targeted drug delivery for cancer therapy:the other side of antibodies" Journal of Hematology & Oncology, vol. 5, No. 70, Nov. 9, 2012 (Nov. 9, 2012).
Gilad, Y.et al. ""Switch off/switch on" regulation of drug cytotoxicity by conjugation to a cell targeting peptide" European Journal of Medicinal Chemistry, vol. 85, Jul. 22, 2014 (Jul. 22, 2014).
International Search Report dated Dec. 14, 2017 in corresponding International Application No. PCT/CN2017/087350, 7 pages.
Supplementary European Search Report and search opinion in EP Application No. 17809717.6, dated Jan. 23, 2020, in 8 pages.
Ahmad Fawzi Hussain: "Specific delivery of therapeutic agents against cancers", Von der Fakult?t f?r Mathematik, Informatik und Naturwissenschaften der RWTH Aachen University zur Erlangung des akademischen Grades eines Doktors der Naturwissenschaften genehmigte Dissertation, Sep. 28, 2012 (Sep. 28, 2012), pp. 1-103, XP05524 8950, Retrieved from the Internet: URL:http://publications. rwth-aachen.de/rec ord/197541/files/4326.pdf [retrieved on Feb. 10, 2016].

(Continued)

*Primary Examiner* — Elly-Gerald Stoica

(74) *Attorney, Agent, or Firm* — Duane Morris LLP

(57) ABSTRACT

The invention relates to antibody fusion proteins. Particularly, the invention relates to antibody fusion proteins for intra-cellular and intra-nucleus drugs delivery. The fusion protein of the invention can be used as a peptide penetration system that specifically binds to various targets for the delivery of effector peptides across a biological barrier.

14 Claims, 11 Drawing Sheets
Specification includes a Sequence Listing.

(56) References Cited

OTHER PUBLICATIONS

Yaghoub Safdari et al: "Use of Single-Chain Antibody Derivatives for Targeted Drug Delivery", Molecular Medicine, vol. 22, No. I, Jan. 1, 2016 (Jan. 1, 2016), pp. 258-270.
Zhang, Jun-Fang, et al. "A cell-penetrating whole molecule antibody targeting intracellular HBx suppresses hepatitis B virus via TRIM21-dependent path562.way." Theranostics 8.2 (2018): 549-562.
Office Action in Taiwan Counterpart Application No. 106118737 dated Apr. 29, 2021, in 12 pages; English translation provided.
Safdari, et al., "Use of single chain antibody derivatives for targeted drug delivery", Mol Med. Sep. 2016, 22:258-270.
Office Action for Chinese patent application No. 201780034897.1 dated Dec. 17, 2021.
Office Action in Japan Counterpart Application No. 2019-516048, dated May 12, 2021, in 8 pages; machine translation provided.
Office Action in Japan Counterpart Application No. 2019-516048, dated Nov. 26, 2021, in 5 pages; machine translation provided.

B

C

SEQUENCE LISTING

<160> NUMBER OF SEQ ID NOS: 26

<210> SEQ ID NO 1
<211> LENGTH: 9
<212> TYPE: PRT
<213> ORGANISM: artificial sequence
<220> FEATURE:
<223> OTHER INFORMATION: synthetic peptide

<400> SEQUENCE: 1

Leu His Cys Lys Ser Phe Ala Ser Gly
1               5

<210> SEQ ID NO 2
<211> LENGTH: 14
<212> TYPE: PRT
<213> ORGANISM: artificial sequence
<220> FEATURE:
<223> OTHER INFORMATION: synthetic peptide

<400> SEQUENCE: 2

Lys Leu Ala Lys Leu Ala Lys Lys Leu Ala Lys Leu Ala Lys
1               5                   10

<210> SEQ ID NO 3
<211> LENGTH: 9
<212> TYPE: PRT
<213> ORGANISM: artificial sequence
<220> FEATURE:
<223> OTHER INFORMATION: synthetic peptide

<400> SEQUENCE: 3

Lys His Ser Ser Gly Cys Ala Phe Leu
1               5

<210> SEQ ID NO 4
<211> LENGTH: 9
<212> TYPE: PRT
<213> ORGANISM: artificial sequence
<220> FEATURE:
<223> OTHER INFORMATION: synthetic peptide

<400> SEQUENCE: 4

Lys His Ser Pro Ala Cys Ala Phe Leu
1               5

<210> SEQ ID NO 5
<211> LENGTH: 7
<212> TYPE: PRT
<213> ORGANISM: artificial sequence
<220> FEATURE:
<223> OTHER INFORMATION: synthetic sequence

<400> SEQUENCE: 5

Lys Pro Leu Gly Leu Ala Arg
1               5

<210> SEQ ID NO 6
<211> LENGTH: 6
<212> TYPE: PRT
<213> ORGANISM: artificial sequence
<220> FEATURE:
<223> OTHER INFORMATION: synthetic sequence

<400> SEQUENCE: 6

Pro Leu Gly Leu Ala Gly
1               5

<210> SEQ ID NO 7
<211> LENGTH: 7
<212> TYPE: PRT
<213> ORGANISM: artificial sequence
<220> FEATURE:
<223> OTHER INFORMATION: synthetic sequence

<400> SEQUENCE: 7

Lys Pro Leu Gly Leu Ala Gly
1               5

<210> SEQ ID NO 8
<211> LENGTH: 1458
<212> TYPE: DNA
<213> ORGANISM: artificial sequence
<220> FEATURE:
<223> OTHER INFORMATION: heavy chain of antibody 3D4KLA

<400> SEQUENCE: 8

```
cagatccagt tggtgcagtc tggacctgag ctgaagaagc tggagagaca gtcaagatc       60 tcctgcaagg cttctgggta taccttcaca actatggaa tgaactgggt gaggcaggct      120
ccaggaaagg ctttaaagtg gatggtctgg atgaacacca cactggaga gtcaatatat      180 gctgaggagt tcaagggacg gtttgtcttc tctttggata cctctgccag tactgcctat      240
ttgcagatca caacctcaa caatgaggac acggctacat atttctgtgc aagatactgg      300
gacacctatt ggggccaagg caccactctc acagtctcct cagctagcac caagggccca      360
tcggtcttcc ccctggcacc ctcctccaag agcacctctg gggcacagc ggccctgggc       420 tgcctggtca aggactactt ccccgaaccg gtgacggtgt cgtggaactc aggcgccctg      480
accagcggcg tgcacacctt cccggctgtc ctacagtcct caggactcta ctccctcagc      540
agcgtggtga ccgtgccctc agcagcttg gcacccaga cctacatctg caacgtgaat       600
cacaagccca gcaacaccaa ggtggacaag aaagcagagc ccaaatcttg tgacaaaact      660
cacacatgcc caccgtgccc agatgacgac gatgatgaca aaccactggg cctggccaga      720
cgccggagaa ggagacgcag gcggagaaaa ctggcaaagc ttgccaagaa actcgccaag      780
cttgctaaac cactgggcct ggcgggcgca cctgaactcc tggggggacc gtcagtcttc      840
ctcttccccc caaaacccaa ggacaccctc atgatctccc ggaccctga ggtcacatgc       900 gtggtggtgg acgtgagcca cgaagaccct gaggtcaagt tcaactggta cgtggacggc      960
gtggaggtgc ataatgccaa gacaaagccg cgggaggagc agtacaacag cacgtaccgt     1020
gtggtcagcg tcctcaccgt cctgcaccag gactggctga atggcaagga ctacaagtgc     1080
aaggtctcca acaaagccct cccagccccc atcgagaaaa ccatctccaa agccaaaggg     1140
cagccccgag aaccacaggt gtacaccctg cccccatccc gggatgagct gaccaggaac     1200
caggtcagcc tgacctgcct ggtcaaaggc ttctatccca gcgacatcgc cgtggagtgg     1260
gagagcaatg ggcagccgga gaacaactac aagaccacgc ctcccgtgct ggactccgac     1320
ggctccttct cctctacag caagctcacc gtggacaaga gcaggtggca gcagggggaac     1380 gtcttctcat gctccgtgat gcatgaggct ctgcacaacc actacacgca gaagagcctc     1440
tccctgtctc cgggtaaa                                                  1458
```

<210> SEQ ID NO 9
<211> LENGTH: 486
<212> TYPE: PRT
<213> ORGANISM: artificial sequence
<220> FEATURE:
<223> OTHER INFORMATION: heavy chain of antibody 3D4KLA

<400> SEQUENCE: 9

| | | | | | | | | | | | | | | |
|---|---|---|---|---|---|---|---|---|---|---|---|---|---|---|
| Gln | Ile | Gln | Leu | Val | Gln | Ser | Gly | Pro | Glu | Leu | Lys | Lys | Pro | Gly | Glu |
| 1 | | | | 5 | | | | | 10 | | | | | 15 | |
| Thr | Val | Lys | Ile | Ser | Cys | Lys | Ala | Ser | Gly | Tyr | Thr | Phe | Thr | Asn | Tyr |
| | | | 20 | | | | | 25 | | | | | 30 | | |
| Gly | Met | Asn | Trp | Val | Arg | Gln | Ala | Pro | Gly | Lys | Ala | Leu | Lys | Trp | Met |
| | | 35 | | | | | 40 | | | | | 45 | | | |
| Val | Trp | Met | Asn | Thr | Asn | Thr | Gly | Glu | Ser | Ile | Tyr | Ala | Glu | Glu | Phe |
| 50 | | | | | 55 | | | | | 60 | | | | | |
| Lys | Gly | Arg | Phe | Val | Phe | Ser | Leu | Asp | Thr | Ser | Ala | Ser | Thr | Ala | Tyr |
| 65 | | | | 70 | | | | | 75 | | | | | 80 | |
| Leu | Gln | Ile | Asn | Asn | Leu | Asn | Asn | Glu | Asp | Thr | Ala | Thr | Tyr | Phe | Cys |
| | | | | 85 | | | | | 90 | | | | | 95 | |
| Ala | Arg | Tyr | Trp | Asp | Thr | Tyr | Trp | Gly | Gln | Gly | Thr | Thr | Leu | Thr | Val |
| | | | 100 | | | | | 105 | | | | | 110 | | |
| Ser | Ser | Ala | Ser | Thr | Lys | Gly | Pro | Ser | Val | Phe | Pro | Leu | Ala | Pro | Ser |
| | | | 115 | | | | | 120 | | | | | 125 | | |
| Ser | Lys | Ser | Thr | Ser | Gly | Gly | Thr | Ala | Ala | Leu | Gly | Cys | Leu | Val | Lys |
| | 130 | | | | | 135 | | | | | 140 | | | | |
| Asp | Tyr | Phe | Pro | Glu | Pro | Val | Thr | Val | Ser | Trp | Asn | Ser | Gly | Ala | Leu |
| 145 | | | | | 150 | | | | | 155 | | | | | 160 |
| Thr | Ser | Gly | Val | His | Thr | Phe | Pro | Ala | Val | Leu | Gln | Ser | Ser | Gly | Leu |
| | | | | 165 | | | | | 170 | | | | | 175 | |
| Tyr | Ser | Leu | Ser | Ser | Val | Val | Thr | Val | Pro | Ser | Ser | Ser | Leu | Gly | Thr |
| | | | 180 | | | | | 185 | | | | | 190 | | |
| Gln | Thr | Tyr | Ile | Cys | Asn | Val | Asn | His | Lys | Pro | Ser | Asn | Thr | Lys | Val |
| | | | 195 | | | | | 200 | | | | | 205 | | |
| Asp | Lys | Lys | Ala | Glu | Pro | Lys | Ser | Cys | Asp | Lys | Thr | His | Thr | Cys | Pro |
| | 210 | | | | | 215 | | | | | 220 | | | | |
| Pro | Cys | Pro | Asp | Asp | Asp | Asp | Asp | Lys | Pro | Leu | Gly | Leu | Ala | Arg |
| 225 | | | | 230 | | | | | 235 | | | | | 240 |
| Arg | Arg | Arg | Arg | Arg | Arg | Arg | Arg | Lys | Leu | Ala | Lys | Leu | Ala | Lys |
| | | | 245 | | | | | 250 | | | | | 255 | |
| Lys | Leu | Ala | Lys | Leu | Ala | Lys | Pro | Leu | Gly | Leu | Ala | Gly | Ala | Pro | Glu |
| | | 260 | | | | | 265 | | | | | 270 | | | |
| Leu | Leu | Gly | Gly | Pro | Ser | Val | Phe | Leu | Phe | Pro | Pro | Lys | Pro | Lys | Asp |
| | | 275 | | | | | 280 | | | | | 285 | | | |
| Thr | Leu | Met | Ile | Ser | Arg | Thr | Pro | Glu | Val | Thr | Cys | Val | Val | Val | Asp |
| | 290 | | | | | 295 | | | | | 300 | | | | |
| Val | Ser | His | Glu | Asp | Pro | Glu | Val | Lys | Phe | Asn | Trp | Tyr | Val | Asp | Gly |
| 305 | | | | | 310 | | | | | 315 | | | | | 320 |
| Val | Glu | Val | His | Asn | Ala | Lys | Thr | Lys | Pro | Arg | Glu | Glu | Gln | Tyr | Asn |
| | | | | 325 | | | | | 330 | | | | | 335 | |
| Ser | Thr | Tyr | Arg | Val | Val | Ser | Val | Leu | Thr | Val | Leu | His | Gln | Asp | Trp |
| | | | 340 | | | | | 345 | | | | | 350 | | |
| Leu | Asn | Gly | Lys | Asp | Tyr | Lys | Cys | Lys | Val | Ser | Asn | Lys | Ala | Leu | Pro |
| | | 355 | | | | | 360 | | | | | 365 | | | |
| Ala | Pro | Ile | Glu | Lys | Thr | Ile | Ser | Lys | Ala | Lys | Gly | Gln | Pro | Arg | Glu |
| | 370 | | | | | 375 | | | | | 380 | | | | |
| Pro | Gln | Val | Tyr | Thr | Leu | Pro | Pro | Ser | Arg | Asp | Glu | Leu | Thr | Arg | Asn |
| 385 | | | | | 390 | | | | | 395 | | | | | 400 |

Gln Val Ser Leu Thr Cys Leu Val Lys Gly Phe Tyr Pro Ser Asp Ile
            405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
            485

<210> SEQ ID NO 10
<211> LENGTH: 642
<212> TYPE: DNA
<213> ORGANISM: artificial sequence
<220> FEATURE:
<223> OTHER INFORMATION: light chain of antibody 3D4KLA, 3D4S9, 3D4rS9,
      3D4rS9-Delta D6, 3D4rS9-A, 3D4rS9-D, 3D4Fc-rS9, 3D4, or 3D4scr

<400> SEQUENCE: 10
gacatcaaga tgacccagtc tccatcttcc atgtatgcat ctctaggaga gagagtcact       60
atcacttgca aggcgagtca ggacattaat agctatttaa gctggttcca gcagaaacca      120
gggaaatctc ctaagaccct gatctatcgt gcaaacagat tggtagatgg ggtcccatca      180
aggttcagtg gcagtggatc tgggcaagat tttctctca ccatcagcag ccttgagtat       240
gaagatatgg gaatttatta ttgtctacag tatgatgagt ttccgtacac gttcggaggg      300
gggaccaagc tggaaatcaa acgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga aaacacaaa gtctacgcct gcgaagtcac ccatcagggc       600
ctgagctcgc ccgtcacaaa gagcttcaac aggggagagt gt                         642

<210> SEQ ID NO 11
<211> LENGTH: 214
<212> TYPE: PRT
<213> ORGANISM: artificial sequence
<220> FEATURE:
<223> OTHER INFORMATION: light chain of antibody 3D4KLA, 3D4S9, 3D4rS9,
      3D4rS9-Delta D6, 3D4rS9-A, 3D4rS9-D, 3D4Fc-rS9, 3D4, or 3D4scr

<400> SEQUENCE: 11

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr

```
                85                  90                  95
Thr Phe Gly Gly Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
            210

<210> SEQ ID NO 12
<211> LENGTH: 1443
<212> TYPE: DNA
<213> ORGANISM: artificial sequence
<220> FEATURE:
<223> OTHER INFORMATION: heavy chain of antibody 3D4S9

<400> SEQUENCE: 12
cagatccagt tggtgcagtc tggacctgag ctgaagaagc tggagagaca agtcaagatc      60
tcctgcaagg cttctgggta taccttcaca aactatggaa tgaactgggt gaggcaggct     120
ccaggaaagg ctttaaagtg gatggtctgg atgaacacca acactggaga gtcaatatat     180
gctgaggagt tcaagggacg gtttgtcttc tctttggata cctctgccag tactgcctat     240
ttgcagatca caaacctcaa caatgaggac acggctacat atttctgtgc aagatactgg     300
gacacctatt ggggccaagg caccactctc acagtctcct cagctagcac caagggccca     360
tcggtcttcc ccctggcacc ctcctccaag agcacctctg gggcacagc ggccctgggc      420 tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttg gcacccaga cctacatctg caacgtgaat      600
cacaagccca gcaacaccaa ggtggacaag aaagcagagc ccaaatcttg tgacaaaact     660
cacacatgcc caccgtgccc agatgacgac gatgatgaca aaccactggg cctggccaga     720
cgccggagaa ggagacgcag gcggagaaaa cattccagcg gctgcgcatt tctgccactg     780
ggcctggcgg gcgcacctga actcctgggg ggaccgtcag tcttcctctt ccccccaaaa     840
cccaaggaca ccctcatgat ctcccggacc cctgaggtca catgcgtggt ggtggacgtg     900
agccacgaag accctgaggt caagttcaac tggtacgtgg acggcgtgga ggtgcataat     960
gccaagacaa agccgcggga ggagcagtac aacagcacgt accgtgtggt cagcgtcctc    1020
accgtcctgc accaggactg gctgaatggc aaggactaca gtgcaaggt ctccaacaaa     1080 gccctcccag ccccccatcga gaaaaccatc tccaaagcca agggcagcc ccgagaacca    1140 caggtgtaca ccctgccccc atcccgggat gagctgacca ggaaccaggt cagcctgacc    1200
tgcctggtca aaggcttcta tcccagcgac atcgccgtgg agtgggagag caatgggcag    1260
ccggagaaca actacaagac cacgcctccc gtgctggact ccgacggctc cttcttcctc    1320
```

```
tacagcaagc tcaccgtgga caagagcagg tggcagcagg ggaacgtctt ctcatgctcc   1380
gtgatgcatg aggctctgca caaccactac acgcagaaga gcctctccct gtctccgggt   1440
aaa                                                                 1443
```

<210> SEQ ID NO 13
<211> LENGTH: 481
<212> TYPE: PRT
<213> ORGANISM: artificial sequence
<220> FEATURE:
<223> OTHER INFORMATION: heavy chain of antibody 3D4S9

<400> SEQUENCE: 13

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Ala Leu Lys Trp Met
        35                  40                  45

Val Trp Met Asn Thr Asn Thr Gly Glu Ser Ile Tyr Ala Glu Glu Phe
    50                  55                  60

Lys Gly Arg Phe Val Phe Ser Leu Asp Thr Ser Ala Ser Thr Ala Tyr
65                  70                  75                  80

Leu Gln Ile Asn Asn Leu Asn Asn Glu Asp Thr Ala Thr Tyr Phe Cys
                85                  90                  95

Ala Arg Tyr Trp Asp Thr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Ala Glu Pro Lys Ser Cys Asp Lys Thr His Thr Cys Pro
    210                 215                 220

Pro Cys Pro Asp Asp Asp Asp Asp Lys Pro Leu Gly Leu Ala Arg
225                 230                 235                 240

Arg Arg Arg Arg Arg Arg Arg Arg Lys His Ser Ser Gly Cys Ala
                245                 250                 255

Phe Leu Pro Leu Gly Leu Ala Gly Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Tyr Arg Val
                325                 330                 335
```

```
Val Ser Val Leu Thr Val Leu His Gln Asp Trp Leu Asn Gly Lys Asp
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Arg Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

<210> SEQ ID NO 14
<211> LENGTH: 1443
<212> TYPE: DNA
<213> ORGANISM: artificial sequence
<220> FEATURE:
<223> OTHER INFORMATION: heavy chain of antibody 3D4rS9

<400> SEQUENCE: 14

```
cagatccagt tggtgcagtc tggacctgag ctgaagaagc tggagagaca agtcaagatc    60
tcctgcaagg cttctgggta taccttcaca aactatggaa tgaactgggt gaggcaggct   120
ccaggaaagg ctttaaagtg gatggtctgg atgaacacca cactggaga gtcaatatat   180
gctgaggagt tcaagggacg gtttgtcttc tctttggata cctctgccag tactgcctat   240
ttgcagatca caaccctcaa caatgaggac acggctacat atttctgtgc aagatactgg   300
gacaccctat tggggccaagg caccactctc acagtctcct cagctagcac caagggccca   360
tcggtcttcc ccctggcacc ctcctccaag agcacctctg ggggcacagc ggccctgggc   420
tgcctggtca aggactactt ccccgaaccg gtgacggtgt cgtggaactc aggcgccctg   480
accagcggcg tgcacacctt cccggctgtc ctacagtcct caggactcta ctccctcagc   540
agcgtggtga ccgtgccctc agcagcttg gcacccaga cctacatctg caacgtgaat   600
cacaagccca gcaacaccaa ggtggacaag aaagcagagc ccaaatcttg tgacaaaact   660
cacacatgcc caccgtgccc agatgacgac gatgatgaca accactggg cctggccaga   720
cgccggagaa ggagacgcag gcggagaaaa cattccccccg cctgcgcatt tctgccactg   780
ggcctggcgg gcgcacctga actcctgggg ggaccgtcag tcttcctctt cccccccaaaa   840
cccaaggaca ccctcatgat ctcccggacc cctgaggtca catgcgtggt ggtggacgtg   900
agccacgaag accctgaggt caagttcaac tggtacgtgg acggcgtgga ggtgcataat   960
gccaagacaa agccgcggga ggagcagtac aacagcacgt accgtgtggt cagcgtcctc  1020
accgtcctgc accaggactg gctgaatggc aaggactaca gtgcaaggt ctccaacaaa  1080
gccctcccag cccccatcga gaaaaccatc tccaaagcca aagggcagcc ccgagaacca  1140
caggtgtaca ccctgccccc atcccgggat gagctgacca ggaaccaggt cagcctgacc  1200
```

```
tgcctggtca aaggcttcta tcccagcgac atcgccgtgg agtgggagag caatgggcag    1260
ccggagaaca actacaagac cacgcctccc gtgctggact ccgacggctc cttcttcctc    1320
tacagcaagc tcaccgtgga caagagcagg tggcagcagg ggaacgtctt ctcatgctcc    1380
gtgatgcatg aggctctgca caaccactac acgcagaaga gcctctccct gtctccgggt    1440
aaa                                                                 1443
```

<210> SEQ ID NO 15
<211> LENGTH: 481
<212> TYPE: PRT
<213> ORGANISM: artificial sequence
<220> FEATURE:
<223> OTHER INFORMATION: heavy chain of antibody 3D4rS9

<400> SEQUENCE: 15

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Ala Leu Lys Trp Met
         35                  40                  45

Val Trp Met Asn Thr Asn Thr Gly Glu Ser Ile Tyr Ala Glu Glu Phe
 50                  55                  60

Lys Gly Arg Phe Val Phe Ser Leu Asp Thr Ser Ala Ser Thr Ala Tyr
 65                  70                  75                  80

Leu Gln Ile Asn Asn Leu Asn Asn Glu Asp Thr Ala Thr Tyr Phe Cys
                 85                  90                  95

Ala Arg Tyr Trp Asp Thr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Ala Glu Pro Lys Ser Cys Asp Lys Thr His Thr Cys Pro
    210                 215                 220

Pro Cys Pro Asp Asp Asp Asp Asp Lys Pro Leu Gly Leu Ala Arg
225                 230                 235                 240

Arg Arg Arg Arg Arg Arg Arg Lys His Ser Pro Ala Cys Ala
                245                 250                 255

Phe Leu Pro Leu Gly Leu Ala Gly Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
```

```
                305                 310                 315                 320
Ala Lys Thr Lys Pro Arg Glu Glu Gln Tyr Asn Ser Thr Tyr Arg Val
                    325                 330                 335

Val Ser Val Leu Thr Val Leu His Gln Asp Trp Leu Asn Gly Lys Asp
                    340                 345                 350

Tyr Lys Cys Lys Val Ser Asn Lys Ala Leu Pro Ala Pro Ile Glu Lys
                    355                 360                 365

Thr Ile Ser Lys Ala Lys Gly Gln Pro Arg Glu Pro Gln Val Tyr Thr
                    370                 375                 380

Leu Pro Pro Ser Arg Asp Glu Leu Thr Arg Asn Gln Val Ser Leu Thr
385                 390                 395                 400

Cys Leu Val Lys Gly Phe Tyr Pro Ser Asp Ile Ala Val Glu Trp Glu
                    405                 410                 415

Ser Asn Gly Gln Pro Glu Asn Asn Tyr Lys Thr Thr Pro Pro Val Leu
                    420                 425                 430

Asp Ser Asp Gly Ser Phe Phe Leu Tyr Ser Lys Leu Thr Val Asp Lys
                    435                 440                 445

Ser Arg Trp Gln Gln Gly Asn Val Phe Ser Cys Ser Val Met His Glu
                    450                 455                 460

Ala Leu His Asn His Tyr Thr Gln Lys Ser Leu Ser Leu Ser Pro Gly
465                 470                 475                 480

Lys

<210> SEQ ID NO 16
<211> LENGTH: 1425
<212> TYPE: DNA
<213> ORGANISM: artificial sequence
<220> FEATURE:
<223> OTHER INFORMATION: heavy chain of antibody 3D4rS9-Delta D6

<400> SEQUENCE: 16
cagatccagt tggtgcagtc tggacctgag ctgaagaagc tggagagaca agtcaagatc      60
tcctgcaagg cttctgggta taccttcaca aactatggaa tgaactgggt gaggcaggct     120
ccaggaaagg ctttaaagtg gatggtctgg atgaacacca cactggagag tcaatatat     180 gctgaggagt tcaagggacg gtttgtcttc tctttggata cctctgccag tactgcctat     240
ttgcagatca caaccctcaa caatgaggac acggctacat atttctgtgc aagatactgg     300
gacacctatt ggggccaagg caccactctc acagtctcct cagctagcac caagggccca     360
tcggtcttcc ccctggcacc ctcctccaag agcacctctg gggcacagc ggccctgggc      420 tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttg gcacccagaa cctacatctg caacgtgaat      600
cacaagccca gcaacaccaa ggtggacaag aaagcagagc ccaaatcttg tgacaaaact     660
cacacatgcc caccgtgccc aaaaccactg gcctggcca gacgccggag aaggagacgc      720
aggcggagaa acattcccc cgcctgcgca tttctgccac tgggcctggc gggcgcacct     780
gaactcctgg gggaccgtc agtcttcctc ttccccccaa acccaaggac acccctcatg     840
atctcccgga cccctgaggt cacatgcgtg gtggtggacg tgagccacga agaccctgag     900
gtcaagttca actggtacgt ggacggcgtg gaggtgcata atgccaagac aaagccgcgg     960
gaggagcagt acaacagcac gtaccgtgtg gtcagcgtcc tcaccgtcct gcaccaggac    1020
tggctgaatg gcaaggacta caagtgcaag gtctccaaca aagccctccc agcccccatc    1080
```

```
gagaaaaccaa tctccaaagc caaagggcag ccccgagaac cacaggtgta caccctgccc    1140
ccatcccggg atgagctgac caggaaccag gtcagcctga cctgcctggt caaaggcttc    1200
tatcccagcg acatcgccgt ggagtgggag agcaatgggc agccggagaa caactacaag    1260
accacgcctc ccgtgctgga ctccgacggc tccttcttcc tctacagcaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaa                   1425
```

<210> SEQ ID NO 17
<211> LENGTH: 475
<212> TYPE: PRT
<213> ORGANISM: artificial sequence
<220> FEATURE:
<223> OTHER INFORMATION: heavy chain of antibody 3D4rS9-Delta D6

<400> SEQUENCE: 17

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Ala Leu Lys Trp Met
        35                  40                  45

Val Trp Met Asn Thr Asn Thr Gly Glu Ser Ile Tyr Ala Glu Glu Phe
    50                  55                  60

Lys Gly Arg Phe Val Phe Ser Leu Asp Thr Ser Ala Ser Thr Ala Tyr
65                  70                  75                  80

Leu Gln Ile Asn Asn Leu Asn Asn Glu Asp Thr Ala Thr Tyr Phe Cys
                85                  90                  95

Ala Arg Tyr Trp Asp Thr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Ala Glu Pro Lys Ser Cys Asp Lys Thr His Thr Cys Pro
    210                 215                 220

Pro Cys Pro Lys Pro Leu Gly Leu Ala Arg Arg Arg Arg Arg Arg Arg
225                 230                 235                 240

Arg Arg Arg Lys His Ser Pro Ala Cys Ala Phe Leu Pro Leu Gly Leu
                245                 250                 255

Ala Gly Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300
```

```
Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
            325                 330                 335

Leu His Gln Asp Trp Leu Asn Gly Lys Asp Tyr Lys Cys Lys Val Ser
        340                 345                 350

Asn Lys Ala Leu Pro Ala Pro Ile Glu Lys Thr Ile Ser Lys Ala Lys
    355                 360                 365

Gly Gln Pro Arg Glu Pro Gln Val Tyr Thr Leu Pro Pro Ser Arg Asp
370                 375                 380

Glu Leu Thr Arg Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 18
<211> LENGTH: 1440
<212> TYPE: DNA
<213> ORGANISM: artificial sequence
<220> FEATURE:
<223> OTHER INFORMATION: heavy chain of antibody 3D4rS9-A

<400> SEQUENCE: 18
cagatccagt tggtgcagtc tggacctgag ctgaagaagc tggagagaca agtcaagatc        60
tcctgcaagg cttctgggta taccttcaca aactatggaa tgaactgggt gaggcaggct       120
ccaggaaagg ctttaaagtg gatggtctgg atgaacacca acactggaga gtcaatatat       180
gctgaggagt tcaagggacg gtttgtcttc tctttggata cctctgccag tactgcctat       240
ttgcagatca caaacctcaa caatgaggac acggctacat atttctgtgc aagatactgg       300
gacacctatt ggggccaagg caccactctc acagtctcct cagctagcac caagggccca       360
tcggtcttcc ccctggcacc ctcctccaag agcacctctg gggcacagc ggccctgggc        420 tgcctggtca aggactactt ccccgaaccg gtgacggtgt cgtggaactc aggcgccctg       480
accagcggcg tgcacacctt cccggctgtc ctacagtcct caggactcta ctccctcagc       540
agcgtggtga ccgtgccctc agcagcttg gcacccaga cctacatctg caacgtgaat        600
cacaagccca gcaacaccaa ggtggacaag aaagcagagc ccaaatcttg tgacaaaact       660
cacacatgcc accgtgccc agcacctgaa ctcctggggg gaccgtcagt cttcctcttc        720 ccccaaaac ccaaggacac cctcatgatc tcccggaccc ctgaggtcac atgcgtggtg        780
gtggacgtga gccacgaaga ccctgaggtc aagttcaact ggtacgtgga cggcgtggag       840
gtgcataatg ccaagacaaa ggacgacgac gatgacgata agcctctggg cctggccaga       900
cggcggagaa gaagaaggcg cagacggaag cacagccctg cctgcgcttt tctgccactg       960
ggcctggcgg gccgggagga gcagtacaac agcacgtacc gtgtggtcag cgtcctcacc      1020
gtcctgcacc aggactggct gaatggcaag gactacaagt gcaaggtctc caacaaagcc      1080
```

```
ctcccagccc ccatcgagaa aaccatctcc aaagccaaag ggcagccccg agaaccacag    1140
gtgtacaccc tgcccccatc ccgggatgag ctgaccagga accaggtcag cctgacctgc    1200
ctggtcaaag gcttctatcc cagcgacatc gccgtggagt gggagagcaa tgggcagccg    1260
gagaacaact acaagaccac gcctcccgtg ctggactccg acggctcctt cttcctctac    1320
agcaagctca ccgtggacaa gagcaggtgg cagcagggga acgtcttctc atgctccgtg    1380
atgcatgagg ctctgcacaa ccactacacg cagaagagcc tctccctgtc tccgggtaaa    1440
```

<210> SEQ ID NO 19
<211> LENGTH: 480
<212> TYPE: PRT
<213> ORGANISM: artificial sequence
<220> FEATURE:
<223> OTHER INFORMATION: heavy chain of antibody 3D4rS9-A

<400> SEQUENCE: 19

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Ala Leu Lys Trp Met
        35                  40                  45

Val Trp Met Asn Thr Asn Thr Gly Glu Ser Ile Tyr Ala Glu Glu Phe
    50                  55                  60

Lys Gly Arg Phe Val Phe Ser Leu Asp Thr Ser Ala Ser Thr Ala Tyr
65                  70                  75                  80

Leu Gln Ile Asn Asn Leu Asn Asn Glu Asp Thr Ala Thr Tyr Phe Cys
                85                  90                  95

Ala Arg Tyr Trp Asp Thr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Ala Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Asp
        275                 280                 285

Asp Asp Asp Asp Asp Lys Pro Leu Gly Leu Ala Arg Arg Arg Arg Arg
    290                 295                 300
```

| | | | | | | | | | | | | |
|---|---|---|---|---|---|---|---|---|---|---|---|---|
|Arg|Arg|Arg|Arg|Arg|Lys|His|Ser|Pro|Ala|Cys|Ala|Phe Leu Pro Leu|
|305| | | |310| | | |315| | | |320|
|Gly|Leu|Ala|Gly|Arg|Glu|Glu|Gln|Tyr|Asn|Ser|Thr|Tyr Arg Val Val|
| | | |325| | | |330| | | |335| |
|Ser|Val|Leu|Thr|Val|Leu|His|Gln|Asp|Trp|Leu|Asn|Gly Lys Asp Tyr|
| | |340| | | |345| | | |350| | |
|Lys|Cys|Lys|Val|Ser|Asn|Lys|Ala|Leu|Pro|Ala|Pro|Ile Glu Lys Thr|
| |355| | | | |360| | | |365| | |
|Ile|Ser|Lys|Ala|Lys|Gly|Gln|Pro|Arg|Glu|Pro|Gln|Val Tyr Thr Leu|
|370| | | |375| | | |380| | | | |
|Pro|Pro|Ser|Arg|Asp|Glu|Leu|Thr|Arg|Asn|Gln|Val|Ser Leu Thr Cys|
|385| | | |390| | | |395| | | |400|
|Leu|Val|Lys|Gly|Phe|Tyr|Pro|Ser|Asp|Ile|Ala|Val|Glu Trp Glu Ser|
| | | |405| | | |410| | | |415| |
|Asn|Gly|Gln|Pro|Glu|Asn|Asn|Tyr|Lys|Thr|Thr|Pro|Pro Val Leu Asp|
| | |420| | | |425| | | |430| | |
|Ser|Asp|Gly|Ser|Phe|Phe|Leu|Tyr|Ser|Lys|Leu|Thr|Val Asp Lys Ser|
| |435| | | |440| | | |445| | | |
|Arg|Trp|Gln|Gln|Gly|Asn|Val|Phe|Ser|Cys|Ser|Val|Met His Glu Ala|
|450| | | |455| | | |460| | | | |
|Leu|His|Asn|His|Tyr|Thr|Gln|Lys|Ser|Leu|Ser|Leu|Ser Pro Gly Lys|
|465| | | |470| | | |475| | | |480|

<210> SEQ ID NO 20
<211> LENGTH: 1440
<212> TYPE: DNA
<213> ORGANISM: artificial sequence
<220> FEATURE:
<223> OTHER INFORMATION: heavy chain of antibody 3D4rS9-D

<400> SEQUENCE: 20

```
cagatccagt tggtgcagtc tggacctgag ctgaagaagc tggagagac agtcaagatc     60
tcctgcaagg cttctgggta taccttcaca aactatggaa tgaactgggt gaggcaggct    120
ccaggaaagg ctttaaagtg gatggtctgg atgaacacca cactggaga gtcaatatat    180
gctgaggagt tcaagggacg gtttgtcttc tctttggata cctctgccag tactgcctat    240
ttgcagatca caaccctcaa caatgaggac acggctacat atttctgtgc aagatactgg    300
gacacctatt ggggccaagg caccactctc acagtctcct cagctagcac caagggccca    360
tcggtcttcc ccctggcacc ctcctccaag agcacctctg gggcacagc ggccctgggc    420
tgcctggtca aggactactt ccccgaaccg gtgacggtgt cgtggaactc aggcgccctg    480
accagcggcg tgcacacctt cccggctgtc ctacagtcct caggactcta ctccctcagc    540
agcgtggtga ccgtgccctc agcagcttg ggcacccaga cctacatctg caacgtgaat    600
cacaagccca gcaacaccaa ggtggacaag aaagcagagc ccaaatcttg tgacaaaact    660
cacacatgcc caccgtgccc agcacctgaa ctcctggggg gaccgtcagt cttcctcttc    720
cccccaaaac ccaaggacac cctcatgatc tcccggaccc ctgaggtcac atgcgtggtg    780
gtggacgacg acgatgacga taagcctctg gcctggcca cggcggag aagaagaagg    840
cgcagacgga agcacagccc tgcctgcgct tttctgccac tgggcctggc gggcgtgagc    900
cacgaagacc ctgaggtcaa gttcaactgg tacgtggacg gcgtggaggt gcataatgcc    960
aagacaaagc cgcgggagga gcagtacaac agcacgtacc gtgtggtcag cgtcctcacc   1020
gtcctgcacc aggactggct gaatggcaag gactacaagt gcaaggtctc caacaaagcc   1080
```

-continued

```
ctcccagccc ccatcgagaa aaccatctcc aaagccaaag ggcagccccg agaaccacag    1140
gtgtacaccc tgcccccatc ccgggatgag ctgaccagga accaggtcag cctgacctgc    1200
ctggtcaaag gcttctatcc cagcgacatc gccgtggagt gggagagcaa tgggcagccg    1260
gagaacaact acaagaccac gcctcccgtg ctggactccg acggctcctt cttcctctac    1320
agcaagctca ccgtggacaa gagcaggtgg cagcagggga acgtcttctc atgctccgtg    1380
atgcatgagg ctctgcacaa ccactacacg cagaagagcc tctccctgtc tccgggtaaa    1440
```

<210> SEQ ID NO 21
<211> LENGTH: 480
<212> TYPE: PRT
<213> ORGANISM: artificial sequence
<220> FEATURE:
<223> OTHER INFORMATION: heavy chain of antibody 3D4rS9-D

<400> SEQUENCE: 21

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Ala Leu Lys Trp Met
        35                  40                  45

Val Trp Met Asn Thr Asn Thr Gly Glu Ser Ile Tyr Ala Glu Glu Phe
    50                  55                  60

Lys Gly Arg Phe Val Phe Ser Leu Asp Thr Ser Ala Ser Thr Ala Tyr
65                  70                  75                  80

Leu Gln Ile Asn Asn Leu Asn Asn Glu Asp Thr Ala Thr Tyr Phe Cys
                85                  90                  95

Ala Arg Tyr Trp Asp Thr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Ala Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Asp Asp Asp Asp Lys Pro Leu Gly Leu
            260                 265                 270

Ala Arg Arg Arg Arg Arg Arg Arg Arg Lys His Ser Pro Ala
        275                 280                 285

Cys Ala Phe Leu Pro Leu Gly Leu Ala Gly Val Ser His Glu Asp Pro
    290                 295                 300
```

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Asp Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
370                 375                 380

Pro Pro Ser Arg Asp Glu Leu Thr Arg Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
450                 455                 460

Leu His Asn His Tyr Thr Gln Lys Ser Leu Ser Leu Ser Pro Gly Lys
465                 470                 475                 480

<210> SEQ ID NO 22
<211> LENGTH: 1425
<212> TYPE: DNA
<213> ORGANISM: artificial sequence
<220> FEATURE:
<223> OTHER INFORMATION: heavy chain of antibody 3D4rFc-rS9

<400> SEQUENCE: 22
cagatccagt tggtgcagtc tggacctgag ctgaagaagc tggagagaca agtcaagatc      60
tcctgcaagg cttctgggta taccttcaca aactatggaa tgaactgggt gaggcaggct     120
ccaggaaagg ctttaaagtg gatggtctgg atgaacacca acactggaga gtcaatatat     180
gctgaggagt tcaagggacg gtttgtcttc tctttggata cctctgccag tactgcctat     240
ttgcagatca caaccctcaa caatgaggac acggctacat atttctgtgc aagatactgg     300
gacaccattt ggggccaagg caccactctc acagtctcct cagctagcac aaagggccca     360
tcggtcttcc ccctggcacc ctcctccaag agcacctctg ggggcacagc ggccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttgg gcacccagac ctacatctg caacgtgaat     600 cacaagccca gcaacaccaa ggtggacaag aaagcagagc ccaaatcttg tgacaaaact     660
cacacatgcc caccgtgccc agcacctgaa ctcctggggg gaccgtcagt cttcctcttc     720
cccccaaaac ccaaggacac cctcatgatc tcccggaccc ctgaggtcac atgcgtggtg     780
gtggacgtga gccacgaaga ccctgaggtc aagttcaact ggtacgtgga cggcgtggag     840
gtgcataatg ccaagacaaa gccgcgggag gagcagtaca acagcacgta ccgtgtggtc     900
agcgtcctca ccgtcctgca ccaggactgg ctgaatggca aggactacaa gtgcaaggtc     960
tccaacaaag cctcccagc ccccatcgag aaaaccatct ccaaagccaa agggcagccc    1020
cgagaaccac aggtgtacac cctgccccca tcccgggatg agctgaccag gaaccaggtc    1080

```
agcctgacct gcctggtcaa aggcttctat cccagcgaca tcgccgtgga gtgggagagc    1140
aatgggcagc cggagaacaa ctacaagacc acgcctcccg tgctggactc cgacggctcc    1200
ttcttcctct acagcaagct caccgtggac aagagcaggt ggcagcaggg gaacgtcttc    1260
tcatgctccg tgatgcatga ggctctgcac aaccactaca cgcagaagag cctctccctg    1320
tctccgggta agacgacga cgatgacgat aagcctctgg gcctggccgg acggcggaga    1380
agaagaaggc gcagacggaa gcacagccct gcctgcgctt ttctg                   1425
```

<210> SEQ ID NO 23
<211> LENGTH: 475
<212> TYPE: PRT
<213> ORGANISM: artificial sequence
<220> FEATURE:
<223> OTHER INFORMATION: heavy chain of antibody 3D4Fc-rS9

<400> SEQUENCE: 23

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Ala Leu Lys Trp Met
        35                  40                  45

Val Trp Met Asn Thr Asn Thr Gly Glu Ser Ile Tyr Ala Glu Glu Phe
    50                  55                  60

Lys Gly Arg Phe Val Phe Ser Leu Asp Thr Ser Ala Ser Thr Ala Tyr
65                  70                  75                  80

Leu Gln Ile Asn Asn Leu Asn Asn Glu Asp Thr Ala Thr Tyr Phe Cys
                85                  90                  95

Ala Arg Tyr Trp Asp Thr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Ala Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300
```

Val Leu His Gln Asp Trp Leu Asn Gly Lys Asp Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Asp Glu Leu Thr Arg Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys Asp Asp Asp Asp
            435                 440                 445

Asp Asp Lys Pro Leu Gly Leu Ala Gly Arg Arg Arg Arg Arg Arg Arg
450                 455                 460

Arg Arg Lys His Ser Pro Ala Cys Ala Phe Leu
465                 470                 475

<210> SEQ ID NO 24
<211> LENGTH: 444
<212> TYPE: PRT
<213> ORGANISM: artificial sequence
<220> FEATURE:
<223> OTHER INFORMATION: heavy chain of antibody 3D4 (anti-DSG2)

<400> SEQUENCE: 24

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Arg Gln Ala Pro Gly Lys Ala Leu Lys Trp Met
            35                  40                  45

Val Trp Met Asn Thr Asn Thr Gly Glu Ser Ile Tyr Ala Glu Glu Phe
        50                  55                  60

Lys Gly Arg Phe Val Phe Ser Leu Asp Thr Ser Ala Ser Thr Ala Tyr
65                  70                  75                  80

Leu Gln Ile Asn Asn Leu Asn Asn Glu Asp Thr Ala Thr Tyr Phe Cys
                85                  90                  95

Ala Arg Tyr Trp Asp Thr Tyr Trp Gly Gln Gly Thr Thr Leu Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
    195                 200                 205

Asp Lys Lys Ala Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
        260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Asp Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
        340                 345                 350

Asp Glu Leu Thr Arg Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
        420                 425                 430

Tyr Thr Gln Lys Ser Leu Ser Leu Ser Pro Gly Lys
        435                 440

<210> SEQ ID NO 25
<211> LENGTH: 1443
<212> TYPE: DNA
<213> ORGANISM: artificial sequence
<220> FEATURE:
<223> OTHER INFORMATION: heavy chain of antibody 3D4scr

<400> SEQUENCE: 25
cagatccagt tggtgcagtc tggacctgag ctgaagaagc ctggagagac agtcaagatc      60
tcctgcaagg cttctgggta taccttcaca aactatggaa tgaactgggt gaggcaggct     120
ccaggaaagg cttttaaagtg gatggtctgg atgaacacca cactggaga gtcaatatat     180 gctgaggagt tcaagggacg gtttgtcttc tctttggata cctctgccag tactgcctat     240
ttgcagatca caacctcaa caatgaggac acggctacat atttctgtgc aagatactgg     300
gacacctatt ggggccaagg caccactctc acagtctcct cagctagcac caagggccca     360
tcggtcttcc ccctggcacc ctcctccaag agcacctctg gggcacagc ggccctgggc     420 tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttg ggcacccaga cctacatctg caacgtgaat     600

```
cacaagccca gcaacaccaa ggtggacaag aaagcagagc ccaaatcttg tgacaaaact    660
cacacatgcc caccgtgccc agatgacgac gatgatgaca aaccactggg cctggccaga    720
cgccggagaa ggagacgcag gcggagactg cattgcaaat cctttgcaag cggcccactg    780
ggcctggcgg gcgcacctga actcctgggg ggaccgtcag tcttcctctt ccccccaaaa    840
cccaaggaca ccctcatgat ctcccggacc cctgaggtca catgcgtggt ggtggacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggactaca gtgcaaggt ctccaacaaa   1080 gccctcccag cccccatcga gaaaaccatc tccaaagcca agggcagcc cgagaaccca   1140 caggtgtaca ccctgccccc atcccgggat gagctgacca ggaaccaggt cagcctgacc   1200
tgcctggtca aaggcttcta tcccagcgac atcgccgtgg agtgggagag caatgggcag   1260
ccggagaaca actacaagac cacgcctccc gtgctggact ccgacggctc cttcttcctc   1320
tacagcaagc tcaccgtgga caagagcagg tggcagcagg ggaacgtctt ctcatgctcc   1380
gtgatgcatg aggctctgca caaccactac acgcagaaga gcctctccct gtctccgggt   1440
aaa                                                                 1443
```

<210> SEQ ID NO 26
<211> LENGTH: 481
<212> TYPE: PRT
<213> ORGANISM: artificial sequence
<220> FEATURE:
<223> OTHER INFORMATION: heavy chain of antibody 3D4scr

<400> SEQUENCE: 26

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Ala Leu Lys Trp Met
        35                  40                  45

Val Trp Met Asn Thr Asn Thr Gly Glu Ser Ile Tyr Ala Glu Glu Phe
    50                  55                  60

Lys Gly Arg Phe Val Phe Ser Leu Asp Thr Ser Ala Ser Thr Ala Tyr
65                  70                  75                  80

Leu Gln Ile Asn Asn Leu Asn Asn Glu Asp Thr Ala Thr Tyr Phe Cys
                85                  90                  95

Ala Arg Tyr Trp Asp Thr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205
```

-continued

```
Asp Lys Lys Ala Glu Pro Lys Ser Cys Asp Lys Thr His Thr Cys Pro
    210                 215                 220

Pro Cys Pro Asp Asp Asp Asp Asp Asp Lys Pro Leu Gly Leu Ala Arg
225                 230                 235                 240

Arg Arg Arg Arg Arg Arg Arg Arg Arg Leu His Cys Lys Ser Phe Ala
                245                 250                 255

Ser Gly Pro Leu Gly Leu Ala Gly Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Asp
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Arg Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

DESMOGLEIN 2 ANTIBODY FUSION PROTEINS FOR DRUG DELIVERY

CROSS-REFERENCE TO RELATED APPLICATIONS

This application is a §371 national stage entry of International Application No. PCT/CN2017/087350, filed Jun. 6, 2017, which claims the benefit of priority to provisional application 62/346,386 filed Jun. 6, 2016, the entire contents of each of which are incorporated herein by reference in their entirety.

FIELD OF THE INVENTION

The invention relates to antibody fusion proteins. Particularly, the invention relates to antibody fusion proteins for intra-cellular and intra-nucleus drugs delivery. The antibody fusion proteins of the invention have dual functional targets to bind the extracellular surface markers and achieve intra-cellular targets regulation.

BACKGROUND OF THE INVENTION

Among targeted therapeutic options, antibody-drug conjugates (ADCs) have emerged as the most promising. ADCs are monoclonal antibodies designed to selectively deliver potent cytotoxic drugs into antigen expressing cells. Several components of an ADC including the selection of the antibody, the linker, the cytotoxic drug payload and the site of attachment used to attach the drug to the antibody are critical to the activity of the ADC. The cytotoxic drugs (or payloads) used to make ADCs are typically conjugated to the antibody through cysteine or lysine residues. This results in ADCs that have a heterogeneous number of drugs per antibody. The number of drugs per antibody commonly referred to as the drug to antibody ratio (DAR), can vary between 0 and 8 drugs for an IgG1 antibody. Antibodies with 0 drugs are ineffective and compete with the ADC for binding to the antigen expressing cells. Antibodies with 8 drugs per antibody have reduced in vivo stability, which may contribute to non-target related toxicities. Even a purified ADC with a uniform stoichiometry would still carry drugs conjugated to multiple sites and therefore be a complex mixture of unique entities. Early heterogeneous ADCs suffered from stability, pharmacokinetic, and efficacy issues that hindered clinical development. Though recent advances in chemical site-selective antibody conjugation, including use of engineered cysteine residues, unnatural amino acids, and enzymatic conjugation through glycotransferases and transglutaminases have led to the creation of more-homogenous ADCs, several differences between the methods exist, including the requirement for genetic modification of antibodies, use of enzymes for conjugation, and conjugation site number/location.

WO 2009/025846 provides activatable binding polypeptides (ABPs), which contain a target binding moiety (TBM), a masking moiety (MM), and a cleavable moiety (CM) and suggests that the ABPs exhibit an activatable conformation such that at least one of the TBMs is less accessible to target when uncleaved than after cleavage of the CM in the presence of a cleaving agent capable of cleaving the CM. US 2016/0185875 discloses a hinge antibody capable of being selectively activated in a target cell or tissue to treat a condition therein. The hinge antibody includes a functional antibody, two inhibitory domains and four cleavable linkers. However, the payloads of the two patent publications cannot achieve a satisfied effect, so there is a need to develop a drug delivery system with higher payload.

SUMMARY OF THE INVENTION

The invention uses antibody fusion proteins comprising an antibody and one or more cell penetrating effector peptide (CPEP), which simultaneously targets to a target of interest and deliver peptide payloads for intra-cellular and intra-nucleus treatment. The antibody fusion proteins of the invention are not only simplify the homogenous production than using chemical modification strategies, but also does not contain any chemical drugs as payloads or modified chemical linkers to conjugate.

The invention provides a fusion protein comprising: (a) an antibody or an antigen binding fragment thereof (Ab), which is capable of targeting an extracellular surface marker; and (b) one or more cell penetrating effector peptide (CPEP) fused to the Ab of (a) or fused inside of the Ab of (a), wherein one CPEP comprises, an optional polyanionic domain (PAD), one or two cleavable linkers (CLs), a polycation domain (PCD) and an effector peptide (EP) in an arrangement of (EP-PCD-CL), (PCD-EP-CL), (EP-PCD-CL-PAD), (PAD-CL-PCD-EP-CL), (CL-PCD-EP), (CL-EP-PCD), (PAD-CL-PCD-EP) or (CL-EP-PCD-CL-PAD), from N-terminus to C-terminus, when the CPEP is fused to the terminus of the Ab of (a), or one CPEP comprises, an optional polyanionic domain (PAD), two cleavable linkers (CLs), a polycation domain (PCD) and an effector peptide (EP) in an arrangement of (CL-PCD-EP-CL), (CL-EP-PCD-CL), (PAD-CL-PCD-EP-CL), (PAD-CL-EP-PCD-CL), (CL-EP-PCD-CL-PAD) or (CL-PCD-EP-CL-PAD), from N-terminus to C-terminus, when the CPEP is fused inside of the Ab with its two terminuses.

In one embodiment, one CPEP comprises an optional polyanionic domain (PAD), one or two cleavable linkers (CLs), a polycation domain (PCD) and an effector peptide binding to an intracellular target (EP) in an arrangement of (EP-PCD-CL), (PCD-EP-CL), (EP-PCD-CL-PAD), (PAD-CL-PCD-EP-CL), (CL-PCD-EP), (CL-EP-PCD), (PAD-CL-PCD-EP) or (CL-EP-PCD-CL-PAD), from N-terminus to C-terminus, when the CPEP is fused to the terminus of the antibody or an antigen binding fragment thereof.

In another embodiment, one CPEP comprises an optional polyanionic domain (PAD), two cleavable linkers (CLs), a polycation domain (PCD) and an effector peptide binding to an intracellular target (EP) in an arrangement of (CL-PCD-EP-CL), (CL-EP-PCD-CL), (PAD-CL-PCD-EP-CL), (PAD-CL-EP-PCD-CL), (CL-EP-PCD-CL-PAD) or (CL-PCD-EP-CL-PAD), from N-terminus to C-terminus, when the CPEP is fused inside of the antibody or an antigen binding fragment thereof with its two terminuses. That is, the CPEP integrates into the antibody or an antigen binding fragment thereof (Ab) in any one of the above-mentioned arrangements. In one embodiment, the CPEP is fused inside of the heavy chain of an Ab.

In a further embodiment, the CPEP is fused to the terminus or inside of the heavy chain of the Ab.

In exemplary embodiments, the preferred antibodies are described in paragraph [0053] herein. In one embodiment, the antibody comprises a heavy chain having the amino acid sequence of SEQ ID NO:24 and a light chain sequence having the amino acid sequence of SEQ ID NO: 11. In some embodiment, the antigen-binding fragment of an antibody is a Fab fragment, a Fab' fragment, a Fd fragment, a Fd' fragment, a Fv fragment, a dAb fragment, a F(ab')$_2$ fragment, a single chain fragment, a diabody, or a linear antibody.

In some embodiments, the one or more CPEPs are fused to the N-terminus or C-terminus of the Ab or fused inside of the Ab.

The PCD has a sequence comprising 5 to 20, or any intermediate range thereof, consecutive basic amino acids. In one embodiment, the polycation peptide is selected from the group consisting of polylysine, polyarginine, polyornithine, polyhistidine, and cationic polysaccharides, or mixtures thereof. In another embodiment, the polycation peptide is a composition comprising at least two of the polycations selected from the group consisting of lysine, arginine, polylysine, polyarginine, polyornithine, polyhistidine, and cationic polysaccharides. In a preferred embodiment, the polycation peptide composition is composed of lysine and arginine. In a further embodiment, the polycation peptides are homopolymers or co-polymers, or mixtures thereof.

The EP is a protein payload binding to the intracellular target. The embodiments of the EP are described in paragraph [0060] herein. The preferred EP and their sequences used in the exemplary fusion protein of the invention are listed in paragraph [0061] herein.

The cleavable linker (CL) of the CPEP of the invention is a cleavable linker comprising a plurality of amino acid residues. The CL may include, for example, between about 4 to about 100 amino acids, or between about 6 to about 30 amino acids. The CL may include amino acid residues and may be a peptide linkage of between about 4 to about 30, or between about 4 to about 10 amino acid residues. The CL is cleavable by conditions found in the cellular environment, such as acidic conditions which may be found near cancerous cells and tissues or a reducing environment, as may be found near hypoxic or ischemic cells and tissues; by proteases or other enzymes found on the surface of cells or released near cells having a condition to be treated, such as diseased, apoptotic or necrotic cells and tissues; or by other conditions or factors. The exemplary enzymes for cleavage of CL include, but are not limited to, those described in paragraph 100691 herein. In some embodiments, the CL are selected from those described in paragraph [0070] herein.

The CPEP can optionally comprise an optional polyanionic domain (PAD). In one embodiment, the CPEP is an activatable cell penetration effector peptide (ACPEP) when the CPEP has a polyanionic domain (PAD). The PAD is a polyanionic peptide with a sequence comprising 4 to 20 acidic amino acids (preferably 5 to 9 acidic amino acids). The PAD is effective to form self-assembled polyanion-polycation interactions to prevent the ACPEP across a cell membrane. In some embodiments, a PAD has a sequence comprising 4 to 20, or any intermediate range thereof, consecutive acidic amino acids.

In some embodiments, when the CPEP is fused to the terminus of the Ab of (a), the fusion protein of the invention has an arrangement of: (EP-PCD-CL)-Ab, (PCD-EP-CL)-Ab, (EP-PCD-CL-PAD)-Ab, (PAD-CL-PCD-EP-CL)-Ab, Ab-(CL-PCD-EP), Ab-(CL-EP-PCD), Ab-(PAD-CL-PCD-EP) or Ab-(CL-EP-PCD-CL-PAD), from N-terminus to C-terminus.

In some other embodiments, when the CPEP is fused inside of the Ab with its two terminuses, the fusion protein of the invention has an arrangement of: $Ab^N$-(CL-PCD-EP-CL)-$Ab^C$, $Ab^N$-(CL-EP-PCD-CL)-$Ab^C$, $Ab^N$-(PAD-CL-PCD-EP-CL)-$Ab^C$, $Ab^N$-(PAD-CL-EP-PCD-CL)-$Ab^C$, $Ab^N$-(CL-EP-PCD-CL-PAD)-$Ab^C$ or $Ab^N$-(CL-PCD-EP-CL-PAD)-$Ab^C$, from N-terminus to C-terminus, wherein $Ab^N$ is the N-terminal fragment of the Ab and $Ab^C$ is the C-terminal fragment of the Ab.

The fusion protein of the invention has dual functional targets to bind the extracellular surface markers and achieve intracellular targets regulation. The effecter peptide of the fusion protein of the invention may be entered into a target cell by cleaving the CL in the presence of particular conditions or in a particular environment. In preferred embodiments, the CL is cleavable under physiological conditions. Cleavage of such the CL may be enhanced or may be effected by particular pathological signals or a particular environment related to cells in which the fusion protein delivery is desired. The CL can be cleaved by a specific enzyme, so that the targeting of cellular uptake to a specific location where such conditions obtain can be achieved. After cleavage of the CL, the PCD-EP or EP-PCD portion of the fusion protein is liberated from the Ab.

In some embodiments, the fusion protein of the invention comprises a heavy chain sequence having the amino acid sequence selected from SEQ ID Nos.9, 13, 15, 17, 19, 21 or 23 and a light chain sequence having the amino acid sequence selected from SEQ ID No. 11.

The invention also provides compositions for use in delivery of an effector peptide into a cell. In one embodiment, the composition comprises the fusion protein of the invention and a pharmacologically suitable carrier.

The invention also provides methods for delivering an effect peptide into a cell or a cell nucleus, comprising administering a fusion protein of the invention or a composition comprising the fusion protein of the invention to a subject.

BRIEF DESCRIPTION OF THE DRAWINGS

FIG. 1 shows a schematic diagram of the MoA (mechanism of action) of the ASC bio-drug. Step 1. Antibody recognized cell surface markers. Step 2. The cleavable linkers inside the CPEP were cleavage by micro-environment proteases (e.g. MMPs and ADAMs etc.), and then switched on the cell penetrating function of CPEP. Step 3. Cytotoxic peptides (the peptides cut down from the ASC bio-drugs) carried by CPP/PCD into cytoplasmic and/or nucleus with disease treatment functions.

FIGS. 2 A to C show MoA studies of ASC bio drugs. A. Flow cytometry were demonstrated ASC bio-drugs recognize target cells. B & C, Using flow cytometry and immunofluorescence, results showed that the polycation domain of 3D4S9 was cleaved and internalized into the human breast adenocarcinoma MCF7 cells.

FIGS. 3 A and B show that 3D4KLA reduce the transformation activity in the human breast adenocarcinoma MCF7 and human non-small cell lung cancer H1299 cells. Decreased soft agar colony formation activity in human breast adenocarcinoma MCF7 (A) and human non-small cell lung cancer H1299 cells (B) treated with 3D4KLA.

FIGS. 4 A to F show that 3D4S9 reduces the transformation activity in the different cell lines. Decreased soft agar colony formation activity in human breast adenocarcinoma MDA-MB-231 (A), human breast adenocarcinoma SKBR3 (B), human breast adenocarcinoma MCF7 (C), human lung carcinoma A549 (D), human non-small cell lung cancer H1299 (E) and human pancreatic carcinoma PANC-1 cells (F) treated with 3D4S9.

FIG. 5 shows that 3D4rS9 reduces the transformation activity in the human lung carcinoma A549 cells. Decreased soft agar colony formation activity in human lung carcinoma A549 cells treated with 3D4rS9.

FIGS. 6 A and B show that 3D4rS9-A reduces the transformation activity in the human breast adenocarcinoma SKBR3 and human lung carcinoma A549 cells. Decreased soft agar colony formation activity in human breast adenocarcinoma SKBR3 (A) and human lung carcinoma A549 cells (B) treated with 3D4rS9-A.

Figure 10:
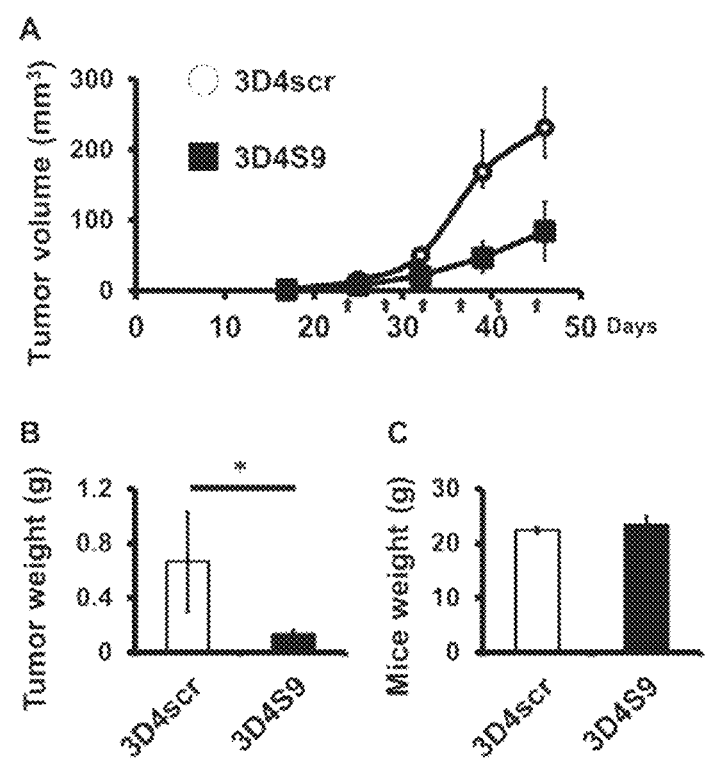

FIGS. 10 A to C show that 3D4S9 reduces xenograft tumor growth in NOD/SCID mice using human pancreatic carcinoma PANC-1 cells. 3D4scr or 3D4S9 are given i.p. twice a week for 3 weeks at the dose of 30 mg/kg. After sacrificing mice, tumors were removed, and their mass was measured. Mice bearing human PANC-1 tumor xenografts treated with 3D4S9 had a tumor volume of 84 (±40) mm3 after three weeks, compared with 231 (±150) mm3 in the 3D4scr control group. The 3D4S9 treatment reduced xenograft tumor volume by 60% (A). Mice bearing human PANC-1 tumor xenografts treated with 3D4S9 had a tumor weight of 0.13 (±0.02) g after three weeks, compared with 0.66 (±0.3) g in the 3D4scr control group. The 3D4S9 treatment reduced xenograft tumor weight by 80% (B). The mice were weighed prior to sacrifice. Mice bearing human PANC-1 tumor xenografts treated with the 3D4scr or 3D4S9 had almost the same body weight (C).

DETAILED DESCRIPTION OF THE INVENTION

In the description that follows, a number of terms are used and the following definitions are provided to facilitate understanding of the claimed subject matter. Terms that are not expressly defined herein are used in accordance with their plain and ordinary meanings.

The antibodies, binding fragments, and polynucleotides described herein are, in many embodiments, described by way of their respective polypeptide or polynucleotide sequences. Unless indicated otherwise, polypeptide sequences are provided in N to C orientation; polynucleotide sequences in 5' to 3' orientation. For polypeptide sequences, the conventional three or one-letter abbreviations for the genetically encoded amino acids may be used.

The abbreviations of the peptides used in the invention are as follows:
Ab: antibody or an antigen binding fragment thereof;
CPEP: penetrating effector peptide;
PAD: polyanionic domain:
CL: cleavable linker:
PCD: polycation domain:
EP: effector peptide:
$Ab^N$: N-terminal fragment of the antibody or an antigen binding fragment thereof (Ab): and
$Ab^C$: C-terminal fragment of the antibody or an antigen binding fragment thereof (Ab).

Unless otherwise specified, the term "a" or "an" means "one or more."

The term "or" is used herein to mean, and is used interchangeably with, the term "and/or", unless context clearly indicates otherwise.

Throughout this application, the term "about" is used to indicate that a value includes the inherent variation of error.

As used herein, the term "payload" refers to EP. The EP is a peptide or protein payloads binding to the intracellular target.

As used herein, the terms "nucleic acid." "nucleic acid sequence," "nucleotide sequence," "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs.

As used herein, the term "amino acid" denotes an organic compound of general formula $NH_2CHRCOOH$ where R can be any organic group. Specifically, the term amino acid may refer to natural and unnatural (man-made) amino acids, such as Aib=alpha-aminoisobutyric acid: tBuAla=Tert-butyl Alanine; Thr-OBzl=Threonine benzyl ester; 5Ava=5-aminovaleric acid; Asp=D=Aspartic Acid: Ala=A=Alanine: Arg=R=Arginine; Asn=N=Asparagine; Gly=G=Glycine; Glu=E=Glutamic Acid: Gln=Q=Glutamine; His=H=Histidine; Ile=I=Isoleucine; Leu=L=Leucine: Lys=K=Lysine; M=Methionine; Mamb=(3-aminomethyl) benzoic acid; Mamp=Met-(3-aminomethyl) phenyl acetic acid; Nle=Norleucine: Nva=Norvaline: Phe=F=Phenylalanine: Pro=P=Proline; Ser=S=Serine; Thr=T=Threonine; Trp=W=Tryptophan; Tyr=Y=Tyrosine; and Val=V=Valine.

As used herein, the term "penetrating peptide" refers to any peptide that facilitates the translocation of a substance across a biological barrier. Examples of biological barriers include, but are not limited to, tight junctions and the plasma membrane. A cell-penetrating peptide (CPP or PCD) is able to penetrate cell membranes and to translocate different cargoes into cells.

As used herein, the terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

As used herein, the term "antibody" refers to intact antibody, monoclonal or polyclonal antibodies. The term "antibody" also encompasses multispecific antibodies such as bispecific antibodies. Human antibodies are usually made of two light chains and two heavy chains each comprising variable regions and constant regions. The light chain variable region comprises 3 CDRs, identified herein as CDRL1 or L1, CDRL2 or L2 and CDRL3 or L3 flanked by framework regions. The heavy chain variable region comprises 3 CDRs, identified herein as CDRH1 or H1, CDRH2 or H2 and CDRH3 or H3 flanked by framework regions. The CDRs of the humanized antibodies of the present invention can be identified using the Kabat and Chotia definitions.

As used herein, the term "activatable" or "switchable" refers to that activatable cell penetration effector peptide (ACPEP) exhibits a first level of non-binding to a target when in a native or uncleaved state (i.e., a first conformation), and a second level of binding to the target in the cleaved state (i.e., a second conformation).

As used herein, the term "administer", "administering" or "to administer" as used herein, refers to the giving or supplying of a medication, including in vivo administration, as well as administration directly to tissue ex vivo.

As used herein, the term "pharmaceutically acceptable" refers to compounds and compositions which are suitable for administration to humans and/or animals without undue adverse side effects such as toxicity, irritation and/or allergic response commensurate with a reasonable benefit/risk ratio.

As used herein, the terms "subject" and "patient" are used interchangeably herein and will be understood to refer to a warm blood animal, particularly a mammal. Non-limiting examples of animals within the scope and meaning of this term include guinea pigs, dogs, cats, rats, mice, horses, goats, cattle, sheep, zoo animals, non-human primates, and humans.

As used herein, the term "effective amount" refers to an amount of a fusion protein or a peptide which is sufficient to exhibit a detectable therapeutic effect without excessive adverse side effects (such as toxicity, irritation and allergic response) commensurate with a reasonable benefit/risk ratio when used in the manner of the inventive concepts.

As used herein, the term "therapeutically effective amount" refers to the amount of a fusion protein or a peptide which is sufficient to exhibit a detectable therapeutic effect, when administered to a mammal or other subject for treating a disease, is sufficient to effect such treatment for the disease.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development: and (c) relieving the disease, i.e., causing regression of the disease.

The invention provides a fusion protein as a peptide penetration system that specifically binds to various targets for the delivery and an effector peptide across a biological barrier. The fusion protein of the invention cures the defects existing in the art such as inefficiency, alteration of the biological properties of the active substance, killing the target cell, irreversible damage of the biological barrier and/or high a risk to be used in human subjects. The fusion protein of the invention exhibits efficient, non-invasive delivery of an unaltered biologically active substance such as an effector peptide.

In one aspect, the invention provides a fusion protein comprising:
(a) an antibody or an antigen binding fragment thereof (Ab), which is capable of targeting an extracellular surface marker; and
(b) one or more cell penetrating effector peptide (CPEP) fused to the Ab of (a) or fused inside of the Ab of (a), wherein one CPEP comprises, an optional polyanionic domain (PAD), one or two cleavable linkers (CLs), a polycation domain (PCD) and an effector peptide (EP) in an arrangement of (EP-PCD-CL), (PCD-EP-CL), (EP-PCD-CL-PAD), (PAD-CL-PCD-EP-CL), (CL-PCD-EP), (CL-EP-PCD), (PAD-CL-PCD-EP) or (CL-EP-PCD-CL-PAD), from N-terminus to C-terminus, when the CPEP is fused to the terminus of the Ab of (a), or one CPEP comprises, an optional polyanionic domain (PAD), two cleavable linkers (CLs), a polycation domain (PCD) and an effector peptide (EP) in an arrangement of (CL-PCD-EP-CL), (CL-EP-PCD-CL). (PAD-CL-PCD-EP-CL), (PAD-CL-EP-PCD-CL), (CL-EP-PCD-CL-PAD) or (CL-PCD-EP-CL-PAD), from N-terminus to C-terminus, when the CPEP is fused inside of the Ab with its two terminuses.

The one or more CPEPs are fused to or fused inside of the antibody or an antigen binding fragment thereof. The antibody or an antigen binding fragment thereof used in the invention specifically binds to a target of interest on any cell or cell population that expresses the target of interest. Exemplary targets include, but are not limited to, amino acid sequences (e.g., polypeptides, peptides, and proteins), polysaccharides, oligosaccharides, carbohydrates, and lipids. Specific non-limiting classes of targets include receptors and antigens. Targets include receptors that bind to antigens, receptors or ligands, including hormones, growth factors, cluster of differentiation (collectively known as CD molecules or CD markers), hormone and growth factor analogues, and fragments of hormones, hormone analogs, growth factors, growth factor analogues, and fragments of growth factors and analogues. Antigen targets include viral, bacterial, fungal and parasite antigens. Antigen targets also include tumor associated antigens (TAAs). In one embodiment, the target is an extracellular target. Exemplary preferred extracellular targets include, but are not limited to those listed in the following table.

alpha4beta1 integrin
alpha4beta7 integrin
alpha5beta1 integrin
alphavbeta3 integrin
alphavbeta5 integrin
calretinin
CD105
CD11a
CD172A
CD19
CD20
CD22
CD25
CD28
CD3
CD30
CD40
CD40L
CD41
CD44
CD52
CD64
CD80
Claudin-3
Claudin-4
c-Met
complement C3
complement C5
CSF1
CSF1R
CTLA-4
CXCR-4
DLL4
DSG2
DSG3
EGFR
EpCAM
EPHA2
ERBB3/HER3
FAP fibroblast activation protein alpha
Fc Fragment of IgE Receptor Ig
FGF-2

FGFR1
FGFR2
FGFR3
FGFR4
Folate receptor
glycoprotein IIb/IIIa
glycoprotein IIb/IIIa receptor
GP130
HER2/neu
HGF
IFN-alpha
IFN-beta
IFN-gamma
IgE
IGF
IL11
IL12
IL13
IL15
IL17
IL18
IL1B
IL1R
IL2
IL21
IL23
IL23R
IL29
IL2R
IL4
IL4R
IL6
Insulin receptor
Jagged1
Jagged2
Lewis(y) antigen
Mesothelin
MUC1
Na/K ATPase
NGF
Notch1
Notch2
Notch3
Notch4
PDGF-AA
PDGF-BB
PDGFR-alpha
PDGFR-beta
Phosphatidylinositol Glycan F (PIGF)
Prostate stem cell antigen (PSCA)
PSMA
RSV F protein
Sphingosine 1 phosphate
TGF-beta
TNF-alpha
TRAIL-R1
TRAIL-R2
Transferrin
Transferrin receptor
TrkA
TrkB
VCAM-1
VEGF-A
VEGF-B
VEGF-C
VEGF-D
VEGFR1
VEGFR2
VEGFR3

Exemplary antibodies binding to the target include, but are not limited to, those listed in the following table.

| Antibody name | Target |
| --- | --- |
| abiciximab | CD41 |
| abrilumab | integrin alpha-4 beta-7 |
| adalimumab | TNF-alpha |
| adecatumumab | EpCAM |
| aflibercept | VEGF |
| alemtuzumab | CD52 |
| amatuximab | mesothelin |
| atezolizumab | PD-L1 |
| avelumab | PD-L1 |
| basiliximab | CD25 |
| bavituximab | phosphatidylserine |
| bevacizumab | VEGF-A |
| catumaxomab | EpCAM, CD3 |
| cetuximab | EGF receptor |
| daclizumab | CD25 |
| denosumab | RANK ligand |
| duligotumab | HER3 |
| eculizumab | Complement protein C5 |
| edrecolomab | EpCAM |
| efalizumab | CD11a |
| elgemtumab | HER3/ErbB3 |
| ertumaxomab | HER2/neu, CD3 |
| etanercept | TNF-alpha |
| etaracizumab | alpha-v beta-3 integrin |
| etrolizumab | beta7 subunit of integrins alpha4beta7 and alphaEbeta7 |
| figitumumab | IGF-1 receptor |
| golimumab | TNF-alpha |
| infliximab | TNF-alpha |
| ipilimumab | CTLA-4 |
| lumretuzumab | ERBB3 |
| mapatumumab | TRAIL-R1 |
| natalizumab | alpha-4 integrin |
| nimotuzumab | EGFR |
| nivolumab | PD-1 |
| omalizumab | IgE Fc region |
| palivizumab | RSV protein F |
| panitumumab | EGFR |
| patritumab | HER3 |
| pembrolizumab | PD-1 |
| pertuzumab | HER2 |
| ranibizumab | VEGF-A |
| rituximab | CD20 |
| secukinumab | IL17A |
| seribantumab | HER3 |
| tanezumab | NGF |
| tocilizumab | IL-6 receptor |
| tositumomab | CD20 |
| trastuzumab | HER2/neu |
| tremelimumab | CTLA-4 |
| ustekinumab | IL-12 and IL-23 |
| vedolizumab | Integrin alpha4beta7 |
| volociximab | alpha5beta1 integrin |
| zalutumumab | EGFR |

In further embodiments, the antibody is atezolizumab, avelumab, pembrolizumab, duligotumab, pertuzumab or zalutumumab, cetuximab, rituximab, trastuzumab. In one embodiment, the antibody comprises a heavy chain having the amino acid sequence of SEQ ID NO:24 and a light chain sequence having the amino acid sequence of SEQ ID NO: 11.

The antigen binding fragment of the antibody refers to a protein that comprises a subset of the components of the full antibody, and retains an antigen-binding property of the antibody. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain. In some embodiments, the antigen-binding fragment of an antibody is a Fab fragment, a Fab' fragment, a Fd fragment, a Fd' fragment, a Fv fragment, a dAb fragment, a F(ab')₂ fragment, a single chain fragment, a diabody, or a linear antibody.

In one embodiment, one CPEP comprises an optional polyanionic domain (PAD), one or two cleavable linkers (CLs), a polycation domain (PCD) and an effector peptide (EP) in an arrangement of (EP-PCD-CL), (PCD-EP-CL), (EP-PCD-CL-PAD), (PAD-CL-PCD-EP-CL), (CL-PCD-EP), (CL-EP-PCD), (PAD-CL-PCD-EP) or (CL-EP-PCD-CL-PAD), from N-terminus to C-terminus, when the CPEP is fused to the terminus of the antibody or an antigen binding fragment thereof.

In another embodiment, one CPEP comprises an optional polyanionic domain (PAD), two cleavable linkers (CLs), a polycation domain (PCD) and an effector peptide (EP) in an arrangement of (CL-PCD-EP-CL), (CL-EP-PCD-CL), (PAD-CL-PCD-EP-CL), (PAD-CL-EP-PCD-CL), (CL-EP-PCD-CL-PAD) or (CL-PCD-EP-CL-PAD), from N-terminus to C-terminus, when the CPEP is fused inside of the antibody or an antigen binding fragment thereof with its two terminuses. That is, the CPEP integrates into the antibody or an antigen binding fragment thereof (Ab) in any one of the above-mentioned arrangements.

The cleavable linker (CL) of the CPEP of the invention is a cleavable linker comprising a plurality of amino acid residues. The CPEP can comprises one or two CLs. The two CLs may be the same or different. When the CPEP does not have a PAD, the CL needs to connect the antibody or an antigen binding fragment thereof with PCD-EP or EP-PCD. When the CPEP has a PAD, the CL serves to connect the acidic portion PAD with basic portion PCD. The CL may include, for example, between about 4 to about 100 amino acids, or between about 6 to about 30 amino acids. The CL may include amino acid residues and may be a peptide linkage of between about 4 to about 30, or between about 4 to about 10 amino acid residues.

The PCD is a polycation peptide having a sequence comprising 5 to 20 basic amino acids (preferably 7-12 basic amino acids), which is effective to transport the CPEP across a membrane of at least one mammalian cell. The polycation peptides are also found to have a nuclear localizing capability. The PCD has a sequence comprising 5 to 20, or any intermediate range thereof, consecutive basic amino acids. In one embodiment, The PCD comprises from 7 to 12 consecutive basic amino acids. In one embodiment, a basic amino acid is positively charged at pH 6.0. In one embodiment, the polycation peptide is selected from the group consisting of polylysine, polyarginine, polyomithine, polyhistidine, and cationic polysaccharides, or mixtures thereof. In another embodiment, the polycation peptide is a composition comprising at least two of the polycations selected from the group consisting of lysine, arginine, polylysine, polyarginine, polyornithine, polyhistidine, and cationic polysaccharides. In a preferred embodiment, the polycation peptide composition is composed of lysine and arginine. In a further embodiment, the polycation peptides are homopolymers or co-polymers, or mixtures thereof. A polycation peptide homopolymer comprises a single repeating unit of the same cation monomer. A polycation peptide co-polymer comprises different cation monomers or different cationic polymers. In one embodiment, a polycation peptide copolymer may comprise a mixture of cation monomers, a mixture of polycation homopolymers or a mixture of polycation co-polymers. In some embodiments, the PCD includes non-standard amino acids, for example, hydroxylysine, desmosine, isodesmosine, or other non-standard amino acids.

The EP is a protein payload binding to the intracellular target. In one embodiment, the EP is a peptide fragment, enzymatic domain of a protein, or a functional protein. Exemplary EPs include, but are not limited to, those listed in the following.

AKT
Amyloid-beta
APAF1
ARF
Bcl-2
BCL9
beta-catenin
BH3 helix
CDKN2B
Cyclosporin A
Dishevelled
E-cadherin
ERK
EZH2
GNAS
GRB7
HIF-1
Histone H3
Histone H4
HSP60
HSP70
HSP90
IKBKG
ITPR3
KLA
LAP
LFA-1
MAPK8IP1
MDM2
MEK
NBS1
P53
PKA
PKC
RAF
Slug
Smac/DIABLO
Stat3
Survivin
XIAP The preferred EP and their sequences used in the exemplary fusion protein of the invention are listed in the following.

| Effector peptide name (PD) | Effector peptide sequence (N' to C' terminal) | Fusion Protein |
|---|---|---|
| Scramble control | L H C K S F A S G (SEQ ID NO: 1) | 3D4scr |
| KLA | K L A K L A K K K L A K L A K (SEQ ID NO: 2) | 3D4KLA |
| S9 | K H S S G C A F L (SEQ ID NO: 3) | 3D4S9 |
| rS9 | K H S P A C A F L (SEQ ID NO: 4) | 3D4rS9, 3D4rS9-A, 3D4rS9-D, 3D4rS9-ΔD6, 3D4Fc-rS9 |

The CPEP can optionally comprise an optional polyanionic domain (PAD). In one embodiment, the CPEP is an activatable cell penetration effector peptide (ACPEP) when the CPEP has a polyanionic domain (PAD). The ACPEP exhibits activatable binding (switchable binding) to a target protein. Generalized cellular uptake of the cell penetrating peptides is blocked by fusing them to a polyanionic peptide domain via a protease-cleavable linker, neutralizing the polycation domain via the formation of an intramolecular hairpin. For specificity, the linker is designed so that it is cleaved by certain enzyme. After administration, the fusion proteins with the ACPEP of the invention travel to the tumor, wherein the ACPEP is cleaved by the proteinases, and accumulate in the target tissue.

The PAD is a polyanionic peptide with a sequence comprising 4 to 20 acidic amino acids (preferably 5 to 9 acidic amino acids). The PAD is effective to form self-assembled polyanion-polycation interactions to prevent the ACPEP across a cell membrane. In some embodiments, a PAD has a sequence comprising 4 to 20, or any intermediate range thereof, consecutive acidic amino acids. In one embodiment, the PAD comprises from 5 to 9 consecutive acidic amino acids. In one embodiment, an acidic amino acid is negatively charged at pH 6.0. In one embodiment, an acidic amino acid has a side chain with a pKa of less than 6.0. Non-limiting examples of acid amino acids include aspartic acid, glutamic acid, phosphoserine, and phosphothreonine. In a specific embodiment, the PAD comprises 5 to 9 consecutive glutamates, aspartates, or a mixture thereof. In some embodiments, the PAD comprises one or more D-amino acids. In a specific embodiment, the PAD consists of D-amino acids. In some embodiments, the PAD is 6 consecutive aspartate. In some embodiments, the PAD includes non-standard amino acids, for example, hydroxylysine, desmosine, isodesmosine, or other non-standard amino acids. Portion A may include modified amino acids.

In some embodiments, when the CPEP is fused to the terminus of the Ab of (a), the fusion protein of the invention has an arrangement of: (EP-PCD-CL)-Ab, (PCD-EP-CL)-Ab, (EP-PCD-CL-PAD)-Ab. (PAD-CL-PCD-EP-CL)-Ab, Ab-(CL-PCD-EP), Ab-(CL-EP-PCD), Ab-(PAD-CL-PCD-EP) or Ab-(CL-EP-PCD-CL-PAD), from N-terminus to C-terminus.

In some other embodiments, when the CPEP is fused inside of the Ab with its two terminuses, the fusion protein of the invention has an arrangement of: $Ab^N$-(CL-PCD-EP-CL)-$Ab^C$, $Ab^N$-(CL-EP-PCD-CL)-$Ab^C$, $Ab^N$-(PAD-CL-PCD-EP-CL)-$Ab^C$, $Ab^N$-(PAD-CL-EP-PCD-CL)-$Ab^C$, $Ab^N$-(CL-EP-PCD-CL-PAD)-$Ab^C$ or $Ab^N$-(CL-PCD-EP-CL-PAD)-$Ab^C$, from N-terminus to C-terminus, wherein $Ab^N$ is the N-terminal fragment of the Ab and $Ab^C$ is the C-terminal fragment of the Ab. In the case that the CPEP fuses inside of the Ab with its two terminuses, the CPEP integrates into an interest position within the Ab so that the fusion protein of the invention comprises from N-terminus to C-terminus, an antibody N-terminal fragment. CPEP and an antibody C-terminal fragment. The sizes of the antibody N-terminal fragment and the antibody C-terminal fragment vary depending on the position where the CPEP integrates into.

In a further embodiment, the CPEP is fused to the terminus or inside of the heavy chain of the Ab.

The fusion protein of the invention has dual functional targets to bind the extracellular surface markers and achieve intracellular targets regulation. The effecter peptide of the fusion protein of the invention may be entered into a target cell by cleaving the CL in the presence of particular conditions or in a particular environment. In preferred embodiments, the CL is cleavable under physiological conditions. Cleavage of such the CL may be enhanced or may be effected by particular pathological signals or a particular environment related to cells in which the fusion protein delivery is desired. The CL can be cleaved by a specific enzyme, so that the targeting of cellular uptake to a specific location where such conditions obtain can be achieved. After cleavage of the CL, the PCD-EP or EP-PCD portion of the fusion protein is liberated from the Ab.

In some embodiments, the CL is cleavable by conditions found in the cellular environment, such as acidic conditions which may be found near cancerous cells and tissues or a reducing environment, as may be found near hypoxic or ischemic cells and tissues: by proteases or other enzymes found on the surface of cells or released near cells having a condition to be treated, such as diseased, apoptotic or necrotic cells and tissues: or by other conditions or factors.

Exemplary enzymes for cleavage of CL include, but are not limited to, those listed in the following.

ADAM10
ADAM12
ADAM15
ADAM17
ADAM9
ADAMTS1
ADAMTS14
ADAMTS2
ADAMTS4
ADAMTS5
Beta-secretase 1
Caspase 1
Caspase 10
Caspase 11
Caspase 12
Caspase 13
Caspase 14
Caspase 2
Caspase 3
Caspase 4
Caspase 5
Caspase 6
Caspase 7
Caspase 8
Caspase 9
Cathepsin A
Cathepsin B
Cathepsin C
Cathepsin D
Cathepsin E
Cathepsin H
Cathepsin K
Cathepsin L
Cathepsin S
Cathepsin Z
FAP
Furin
Granzyme B
Human neutrophil elastase
Legumain
Matriptase 1
Matriptase 2
Meprin A
Meprin B
MMP1
MMP10
MMP11
MMP12
MMP13
MMP14
MMP15
MMP16
MMP17
MMP19
MMP2
MMP20
MMP23
MMP24

MMP25
MMP26
MMP28
MMP3
MMP7
MMP8
MMP9
Neprilysin
Plasmin
PSA
PSMA
S3-4A Serine Protease
Serine protease hepsin
TACE
TMPRSS2
TMPRSS4
uPA The preferred CL and their sequences used in the exemplary fusion protein of the invention are listed in the following.

| Cleavable linker (CL) | Cleavable linker sequence (N' to C' terminal) | Fusion Protein |
|---|---|---|
| CL1 | KPLGLAR (SEQ ID NO: 5) | 3D4scr, 3D4KLA, 3D4S9, 3D4rS9, 3D4rS9-A, 3D4rS9-D, 3D4rS9-ΔD6 |
| CL2 | PLGLAG (SEQ ID NO: 6) | 3D4scr, 3D4KLA, 3D4S9, 3D4rS9, 3D4rS9-A, 3D4rS9-D, 3D4rS9-ΔD6 |
| CL3 | KPLGLAG (SEQ ID NO: 7) | 3D4Fc-rS9 |

In some embodiments, the fusion proteins of the invention are shown in the table below. The nucleotide and amino acid sequences of each fusion protein are also listed in the table below. Accordingly, in some embodiments, the fusion protein of the invention comprises a heavy chain sequence having the amino acid sequence selected from SEQ ID Nos. 9, 13, 15, 17, 19, 21 and 23, and a light chain sequence having the amino acid sequence selected from SEQ ID No. 11. Accordingly, the fusion protein of the invention comprises:

3D4KLA: a heavy chain having the amino acid sequence of SEQ ID NO:9 and a light chain sequence having the amino acid sequence of SEQ ID NO: 11;

3D4S9: a heavy chain having the amino acid sequence of SEQ ID NO: 13 and a light chain sequence having the amino acid sequence of SEQ ID NO: 11;

3D4rS9: a heavy chain having the amino acid sequence of SEQ ID NO: 15 and a light chain sequence having the amino acid sequence of SEQ ID NO: 11;

3D4rS9-ΔD6: a heavy chain having the amino acid sequence of SEQ ID NO: 17 and a light chain sequence having the amino acid sequence of SEQ ID NO: 11;

3D4rS9-A: a heavy chain having the amino acid sequence of SEQ ID NO: 19 and a light chain sequence having the amino acid sequence of SEQ ID NO: 11;

3D4rS9-D: a heavy chain having the amino acid sequence of SEQ ID NO:21 and a light chain sequence having the amino acid sequence of SEQ ID NO: 11; or 3D4Fc-rS9: a heavy chain having the amino acid sequence of (SEQ ID NO:23) and a light chain sequence having the amino acid sequence of SEQ ID NO: 11.

| Antibody | Nucleic acid sequence and amino acid for heavy and light chain |
|---|---|
| 3D4KLA | Heavy chain |

```
cagatccagttggtgcagtctggacctgagctgaagaagcctggagagacagtcaag
atctcctgcaaggcttctgggtataccttcacaaactatggaatgaactgggtgagg
caggctccaggaaaggctttaaagtggatggtctggatgaacaccaacactggagag
tcaatatatgctgaggagttcaagggacggtttgtcttctctttggatacctctgcc
agtactgcctatttgcagatcaacaacctcaacaatgaggacacggctacatatttc
tgtgcaagatactgggacacctattggggccaaggcaccactctcacagtctcctca
gctagcaccaagggcccatcggtcttccccctggcaccctcctccaagagcacctct
gggggcacagcggccctgggctgcctggtcaaggactacttccccgaaccggtgacg
gtgtcgtggaactcaggcgccctgaccagcggcgtgcacaccttcccggctgtccta
cagtcctcaggactctactccctcagcagcgtggtgaccgtgccctccagcagcttg
ggcacccagacctacatctgcaacgtgaatcacaagcccagcaacaccaaggtggac
aagaaagcagagcccaaatcttgtgacaaaactcacacatgcccaccgtgcccagat
gacgacgatgatgacaaaccactgggcctggccagacgccggagaaggagacgcagg
cggagaaaactggcaaagcttgccaagaaactcgccaagcttgctaaaccactgggc
ctggcgggcgcacctgaactcctgggggaccgtcagtcttcctcttccccccaaaa
cccaaggacacccctcatgatctcccggacccctgaggtcacatgcgtggtggtggac
gtgagccacgaagaccctgaggtcaagttcaactggtacgtggacggcgtggaggtg
cataatgccaagacaaagccgcgggaggagcagtacaacagcacgtaccgtgtggtc
agcgtcctcaccgtcctgcaccaggactggctgaatggcaaggactacaagtgcaag
gtctccaacaaagcctcccagccccatcgagaaaccatctccaaagccaaaggg
cagccccgagaaccacaggtgtacaccctgccccatcccgggatgagctgaccagg
aaccaggtcagcctgacctgcctggtcaaaggcttctatcccagcgacatcgccgtg
gagtgggagagcaatgggcagccggagaacaactacaagaccacgcctcccgtgctg
gactccgacggctccttcttcctctacagcaagctcaccgtggacaagagcaggtgg
cagcaggggaacgtcttctcatgctccgtgatgcatgaggctctgcacaaccactac
acgcagaagagcctctccctgtctccgggtaaa (SEQ ID NO: 8)
```

Q I Q L V Q S G P E L K K P G E T V K I S C K A S G Y T F
T N Y G M N W V R Q A P G K A L K W M V W M N T N T G E S
I Y A E E F K G R F V F S L D T S A S T A Y L Q I N N L N
N E D T A T Y F C A R Y W D T Y W G Q G T T L T V S S A S
T K G P S V F P L A P S S K S T S G G T A A L G C L V K D

| Antibody | Nucleic acid sequence and amino acid for heavy and light chain |
|---|---|
| | Y F P E P V T V S W N S G A L T S G V H T F P A V L Q S S<br>G L Y S L S S V V T V P S S S L G T Q T Y I C N V N H K P<br>S N T K V D K K A E P K S C D K T H T C P P C P <u>D D D D</u><br><u>D K P L G L A R</u> R R R R R R R R R K L A K L A K K L A K L<br>A K P L G L A G A P E L L G G P S V F L F P P K P K D T L<br><br>M I S R T P E V T C V V V D V S H E D P E V K F N W Y V D<br>G V E V H N A K T K P R E E Q Y N S T Y R V V S V L T V L<br>H Q D W L N G K D Y K C K V S N K A L P A P I E K T I S K<br>A K G Q P R E P Q V Y T L P P S P D E L T R N Q V S L T C<br>L V K G F Y P S D I A V E W E S N G Q P E N N Y K T T P P<br>V L D S D G S F F L Y S K L T V D K S R W Q Q G N V F S C<br>S V M H E A L H N H Y T Q K S L S L S P G K (SEQ ID NO: 9) |
| | Light chain |
| | Gacatcaagatgacccagtctccatcttccatgtatgcatctctaggagagagagtc<br>actatcacttgcaaggcgagtcaggacattaatagctatttaagctggttccagcag<br>aaaccagggaaatctcctaagaccctgatctatcgtgcaaacagattggtagatggg<br>gtcccatcaaggttcagtggcagtggatctgggcaagattttctctcaccatcagc<br>agccttgagtatgaagatatgggaatttattattgtctacagtatgatgagtttccg<br>tacacgttcggaggggggaccaagctggaaatcaaacgtacggtggctgcaccatct<br>gtcttcatcttcccgccatctgatgagcagttgaaatctggaactgcctctgttgtg<br>tgcctgctgaataacttctatcccagagaggccaaagtacagtggaaggtggataac<br>gccctccaatcgggtaactcccaggagagtgtcacagagcaggacagcaaggacagc<br>acctacagcctcagcagcaccctaacgctgagcaaagcagactacgagaaacacaaa<br>gtctacgcctgcgaagtcacccatcagggcctgagctcgcccgtcacaaagagcttc<br>aacaggggagagtgt (SEQ ID NO: 10)<br><br>D I K M T Q S P S S M Y A S L G E R V T I T C K A S Q D I<br>N S Y L S W F Q Q K P G K S P K T L I Y R A N R L V D G V<br>P S R F S G S G S G Q D F S L T I S S L E Y E D M G I Y Y<br>C L Q Y D E F P Y T F G G G T K L E I K R T V A A P S V F<br>I F P P S D E Q L K S G T A S V V C L L N N F Y P R E A K<br>V Q W K V D N A L Q S G N S Q E S V T E Q D S K D S T Y S<br>L S S T L T L S K A D Y E K H K V Y A C E V T H Q G L S S<br>P V T K S F N R G E C (SEQ ID NO: 11) |
| 3D4S9 | Heavy chain |
| | cagatccagttggtgcagtctggacctgagctgaagaagcctggagagacagtcaag<br>atctcctgcaaggcttctgggtataccttcacaaactatggaatgaactgggtgagg<br>caggctccaggaaaggctttaaagtggatggtctggatgaacaccaacactggagag<br>tcaatatatgctgaggagttcaaggacggttttgtcttctctttggatacctctgcc<br>agtactgcctatttgcagatcaacaacctcaacaatgaggacacggctacatatttc<br>tgtgcaagatactgggacacctattggggccaaggcaccactctcacagtctcctca<br>gctagcaccaagggcccatcggtcttccccctggcaccctcctccaagagcacctct<br>gggggcacagcggccctgggctgcctggtcaaggactacttccccgaaccggtgacg<br>gtgtcgtggaactcaggcgccctgaccagcggcgtgcacaccttcccggctgtccta<br>cagtcctcaggactctactccctcagcagcgtggtgaccgtgccctccagcagcttg<br>ggcacccagacctacatctgcaacgtgaatcacaagcccagcaacaccaaggtggac<br>aagaaagcagagcccaaatcttgtgacaaaactcacacatgcccaccgtgcccagat<br>gacgacgatgatgacaaaccactgggcctggcagacgccggagaaggagacgcagg<br>cggagaaacattccagcggctgcgcatttctgccactgggcctggcgggcgcacct<br>gaactcctggggggaccgtcagtcttcctcttcccccaaaacccaaggacaccctc<br>atgatctcccggacccctgaggtcacatgcgtggtggtggacgtgagccacgaagac<br>cctgaggtcaagttcaactggtacgtggacggcgtggaggtgcataatgccaagaca<br>aagccgcgggaggagcagtacaacagcacgtaccgtgtggtcagcgtcctcaccgtc<br>ctgcaccaggactggctgaatggcaaggactacaagtgcaaggtctccaacaaagcc<br>ctcccagcccccatcgagaaaaccatctccaaagccaaaggtgcagccccgagaacca<br>caggtgtacaccctgcccccatcccgggatgagctgaccaggaaccaggtcagcctg<br>acctgcctggtcaaaggcttctatcccagcgacatcgccgtggagtgggagagcaat<br>gggcagccggagaacaactacaagaccacgcctcccgtgctggactccgacggctcc<br>ttcttcctctacagcaagctcaccgtggacaagagcaggtggcagcaggggaacgtc<br>ttctcatgctccgtgatgcatgaggctctgcacaaccactacacgcagaagagcctc<br>tccctgtctccgggtaaa (SEQ ID NO: 12)<br><br>Q I Q L V Q S G P E L K K P G E T V K I S C K A S G Y T F<br>T N Y G M N W V R Q A P G K A L K W M V W M N T N T G E S<br>I Y A E E F K G R F V F S L D T S A S T A Y L Q I N N L N<br>N E D T A T Y F C A R Y W D T Y W G Q G T T L T V S S A S<br>T K G P S V F P L A P S S K S T S G G T A A L G C L V K D<br>Y F P E P V T V S W N S G A L T S G V H T F P A V L Q S S<br>G L Y S L S S V V T V P S S S L G T Q T Y I C N V N H K P<br>S N T K V D K K A E P K S C D K T H T C P P C P <u>D D D D</u><br><u>D K P L G L A R</u> R R R R R R R R R K H S S G C A F L P L G |

| Antibody | Nucleic acid sequence and amino acid for heavy and light chain |
|---|---|
| | <u>L A G</u> A P E L L G G P S V F L P P K P K D T L M I S R T<br>P E V T C V V V D V S H E D P E V K F N W Y V D G V E V H<br>N A K T K P R E E Q Y N S T Y R V V S V L T V L H Q D W L<br>N G K D Y K C K V S N K A L P A P I E K T I S K A K G Q P<br>R E P Q V Y T L P P S R D E L T R N Q V S L T C L V K G F<br>Y P S D I A V E W E S N G Q P E N N Y K T T P P V L D S D<br>G S F F L Y S K L T V D K S R W Q Q G N V F S C S V M H E<br>A L H N H Y T Q K S L S L S P G K (SEQ ID NO: 13) |

Light Chain

Gacatcaagatgacccagtctccatcttccatgtatgcatctctaggagagagagtc
actatcacttgcaaggcgagtcaggacattaatagctatttaagctggttccagcag
aaaccagggaaatctcctaagaccctgatctatcgtgcaaacagattggtagatggg
gtcccatcaaggttcagtggcagtggatctgggcaagattttctctccaccatcagc
agccttgagtatgaagatatgggaatttattattgtctacagtatgatgagtttccg
tacacgttcggagggggaccaagctggaaatcaaacgtacggtggctgcaccatct
gtcttcatcttcccgccatctgatgagcagttgaaatctggaactgcctctgttgtg
tgcctgctgaataacttctatcccagagaggccaaagtacagtggaaggtggataac
gccctccaatcgggtaactcccaggagagtgtcacagagcaggacagcaaggacagc
acctacagcctcagcagcaccctaacgctgagcaaagcagactacgagaaacacaaa
gtctacgcctgcgaagtcacccatcagggcctgagctcgcccgtcacaaagagcttc
aacaggggagagtgt (SEQ ID NO: 10)

D I K M T Q S P S S M Y A S L G E R V T I T C K A S Q D I
N S Y L S W F Q Q K P G K S P K T L I Y R A N R L V D G V
P S R F S G S G S G Q D F S L T I S S L E Y E D M G I Y Y
C L Q Y D E F P Y T F G G G T K L E I K R T V A A P S V F
I F P P S D E Q L K S G T A S V V C L L N N F Y P R E A K
V Q W K V D N A L Q S G N S Q E S V T E Q D S K D S T Y S
L S S T L T L S K A D Y E K H K V Y A C E V T H Q G L S S
P V T K S F N R G E C (SEQ ID NO: 11)

| 3D4rS9 | Heavy chain |
|---|---|
| | cagatccagttggtgcagtctggacctgagctgaagaagcctggagagacagtcaag<br>atctcctgcaaggcttctgggtataccttcacaaactatggaatgaactgggtgagg<br>caggctccaggaaaggctttaaagtggatggtctggatgaacaccaacactggagag<br>tcaatatatgctgaggagttcaagggacggtttgtcttctctttggatacctctgcc<br>agtactgcctatttgcagatcaacaacctcaacaatgaggacacggctacatatttc<br>tgtgcaagatactgggacacctattggggccaaggcaccactctcacagtctcctca<br>gctagcaccaagggcccatcggtcttccccctggcaccctcctccaagagcacctct<br>ggggg cacagcggccctgggctgcctggtcaaggactacttccccgaaccggtgacg<br>gtgtcgtggaactcaggcgccctgaccagcggcgtgcacaccttcccggctgtccta<br>cagtcctcaggactctactccctcagcagcgtggtgaccgtgccctccagcagcttg<br>ggcacccagacctacatctgcaacgtgaatcacaagcccagcaacaccaaggtggac<br>aagaaagcagagcccaaatcttgtgacaaaactcacacatgcccaccgtgcccagat<br>gacgacgatgatgacaaaccactgggcctggccagacgccgagaaggagacgcagg<br>cggagaaaacattccagcggctgcgcatttctgccactgggcctggcgggcgcacct<br>gaactcctgggggaccgtcagtcttcctcttccccccaaaacccaaggacaccctc<br>atgatctcccggacccctgaggtcacatgcgtggtggtggacgtgagccacgaagac<br>cctgaggtcaagttcaactggtacgtggacggcgtggaggtgcataatgccaagaca<br>aagccgcgggaggagcagtacaacagcacgtaccgtgtggtcagcgtcctcaccgtc<br>ctgcaccaggactggctgaatggcaaggactacaagtgcaaggtctccaacaaagcc<br>ctcccagcccccatcgagaaaaccatctccaaagccaaagggcagccccgagaacca<br>caggtgtacaccctgcccccatcccgggatgagctgaccaggaaccaggtcagcctg<br>acctgcctggtcaaaggcttctatcccagcgacatcgccgtggagtgggagagcaat<br>gggcagccggagaacaactacaagaccacgcctcccgtgctggactccgacggctcc<br>ttcttcctctacagcaagctcaccgtggacaagagcaggtggcagcaggggaacgtc<br>ttctcatgctccgtgatgcatgaggctctgcacaaccactacacgcagaagagcctc<br>tccctgtctccgggtaaa (SEQ ID NO: 14) |

Q I Q L V Q S G P E L K K P G E T V K I S C K A S G Y T F
T N Y G M N W V R Q A P G K A L K W M V W M N T N T G E S
I Y A E E F K G R F V F S L D T S A S T A Y L Q I N N L N
N E D T A T Y F C A R Y W D T Y W G Q G T T L T V S S A S
T K G P S V F P L A P S S K S T S G G T A A L G C L V K D
Y F P E P V T V S W N S G A L T S G V H T F P A V L Q S S
G L Y S L S S V V T V P S S S L G T Q T Y I C N V N H K P
S N T K V D K K A E P K S C D K T H T C P P C P <u>D D D D D</u>
<u>D K P L G L A R</u> <u>R R R R R R R R R</u> <u>K H S S G C A F L P L G</u>

<u>L A G</u> A P E L L G G P S V F L P P K P K D T L M I S R T
P E V T C V V V D V S H E D P E V K F N W Y V D G V E V H
N A K T K P R E E Q Y N S T Y R V V S V L T V L H Q D W L

| Antibody | Nucleic acid sequence and amino acid for heavy and light chain |
|---|---|
| | N G K D Y K C K V S N K A L P A P I E K T I S K A K G Q P<br>R E P Q V Y T L P P S R D E L T R N Q V S L T C L V K G F<br>Y P S D I A V E W E S N G Q P E N N Y K T T P P V L D S D<br>G S F F L Y S K L T V D K S R W Q Q G N V F S C S V M H E<br>A L H N H Y T Q K S L S L S P G K (SEQ ID NO: 15) |

Light Chain

Gacatcaagatgacccagtctccatcttccatgtatgcatctctaggagagagagtc
actatcacttgcaaggcgagtcaggacattaatagctatttaagctggttccagcag
aaaccagggaaatctcctaagaccctgatctatcgtgcaaacagattggtagatggg
gtcccatcaaggttcagtggcagtggatctgggcaagattttctctcaccatcagc
agccttgagtatgaagatatgggaatttattattgtctacagtatgatgagtttccg
tacacgttcggaggggggaccaagctggaaatcaaacgtacggtggctgcaccatct
gtcttcatcttcccgccatctgatgagcagttgaaatctggaactgcctctgttgtg
tgcctgctgaataacttctatcccagagaggccaaagtacagtggaaggtggataac
gccctccaatcgggtaactcccaggagagtgtcacagagcaggacagcaaggacagc
acctacgcctcagcagcacccctaacgctgagcaaagcagactacgagaaacacaaa
gtctacgcctgcgaagtcacccatcagggcctgagctcgcccgtcacaaagagcttc
aacaggggagagtgt (SEQ ID NO: 10)

D I K M T Q S P S S M Y A S L G E R V T I T C K A S Q D I
N S Y L S W F Q Q K P G K S P K T L I Y R A N R L V D G V
P S R F S G S G S G Q D F S L T I S S L E Y E D M G I Y Y
C L Q Y D E F P Y T F G G G T K L E I K R T V A A P S V F
I F P P S D E Q L K S G T A S V V C L L N N F Y P R E A K
V Q W K V D N A L Q S G N S Q E S V T E Q D S K D S T Y S
L S S T L T L S K A D Y E K H K V Y A C E V T H Q G L S S
P V T K S F N R G E C (SEQ ID NO: 11)

| 3D4rS9-ΔD6 | Heavy chain |
|---|---| cagatccagttggtgcagtctggacctgagctgaagaagcctggagagacagtcaag
atctcctgcaaggcttctgggtataccttcacaaactatggaatgaactgggtgagg
caggctccaggaaaggctttaaagtggatggtctggatgaacaccaacactggagag
tcaatatatgctgaggagttcaagggacggtttgtcttctctttggatacctctgcc
agtactgcctatttgcagatcaacaacctcaacaatgaggacacggctacatattc
tgtgcaagatactgggacacctattggggccaaggcaccactctcacagtctcctca
gctagcaccaagggcccatcggtcttccccctggcaccctcctccaagagcacctct
gggggcacagcggccctgggctgcctggtcaaggactacttccccgaaccggtgacg
gtgtcgtggaactcaggcgccctgaccagcggcgtgcacaccttcccggctgtccta
cagtcctcaggactctactccctcagcagcgtggtgaccgtgccctccagcagcttg
ggcacccagacctacatctgcaacgtgaatcacaagcccagcaacaccaaggtggac
aagaaagcagagcccaaatcttgtgacaaaactcacacatgcccaccgtgcccagat
gacgacgatgatgacaaaaccactgggcctggcacagacgccggagaaggagacgcagg
cggagaaaacattccagcggctgcgcatttctgccactgggcctggcgggcgcacct
gaactcctggggggaccgtcagtcttcctcttccccccaaaacccaaggacaccctc
atgatctcccggacccctgaggtcacatgcgtggtggtggacgtgagccacgaagac
cctgaggtcaagttcaactggtacgtggacggcgtggaggtgcataatgccaagaca
aagccgcgggaggagcagtacaacagcacgtaccgtgtggtcagcgtcctcaccgtc
ctgcaccaggactggctgaatggcaaggactacaagtgcaaggtctccaacaaagcc
ctcccagcccccatcgagaaaaccatctccaaagccaaagggcagccccgagaacca
caggtgtacaccctgcccccatcccgggatgagctgaccaagaaccaggtcagcctg
acctgcctggtcaaaggcttctatcccagcgacatcgccgtggagtgggagagcaat
gggcagccggagaacaactacaagaccacgcctcccgtgctggactccgacggctcc
ttcttcctctacagcaagctcaccgtggacaagagcaggtggcagcaggggaacgtc
ttctcatgctccgtgatgcatgaggctctgcacaaccactacacgcagaagagcctc
tccctgtctccgggtaaa (SEQ ID NO: 16)

Q I Q L V Q S G P E L K K P G E T V K I S C K A S G Y T F
T N Y G M N W V R Q A P G K A L K W M V W M N T N T G E S
I Y A E E F K G R F V F S L D T S A S T A Y L Q I N N L N
N E D T A T Y F C A R Y W D T Y W G Q G T T L T V S S A S
T K G P S V F P L A P S S K S T S G G T A A L G C L V K D
Y F P E P V T V S W N S G A L T S G V H T F P A V L Q S S
G L Y S L S S V V T V P S S S L G T Q T Y I C N V N H K P
S N T K V D K K A E P K S C D K T H T C P P C P K P L G L
A R R R R R R R R R K H S P A C A F L P L G L A G A P E
L L G G P S V F L F P P K P K D T L M I S R T P E V T C V
V V D V S H E D P E V K F N W Y V D G V E V H N A K T K P
R E E Q Y N S T Y R V V S V L T V L H Q D W L N G K E Y K
C K V S N K A L P A P I E K T I S K A K G Q P R E P Q V Y
T L P P S R D E L T R N Q V S L T C L V K G F Y P S D I A
V E W E S N G Q P E N N Y K T T P P V L D S D G S F F L Y
S K L T V D K S R W Q Q G N V F S C S V M H E A L H N H Y
T Q K S L S L S P G K (SEQ ID NO: 17)

| Antibody | Nucleic acid sequence and amino acid for heavy and light chain |
|---|---|
| | Light chain |
| | Gacatcaagatgacccagtctccatcttccatgtatgcatctctaggagagagtc<br>actatcacttgcaaggcgagtcaggacattaatagctatttaagctggttccagcag<br>aaaccagggaaatctcctaagaccctgatctatcgtgcaaacagattggtagatggg<br>gtcccatcaaggttcagtggcagtggatctgggcaagattttctctcaccatcagc<br>agccttgagtatgaagatatgggaatttattattgtctacagtatgatgagtttccg<br>tacacgttcggaggggggaccaagctggaaatcaaacgtacggtggctgcaccatct<br>gtcttcatcttcccgccatctgatgagcagttgaaatctggaactgcctctgttgtg<br>tgcctgctgaataacttctatcccagagaggccaaagtacagtggaaggtggataac<br>gcccctccaatcgggtaactcccaggagagtgtcacagagcaggacagcaaggacagc<br>acctacagcctcagcagcacccctaacgctgagcaaagcagactacgagaaacacaaa<br>gtctacgcctgcgaagtcacccatcagggcctgagctcgcccgtcacaaagagcttc<br>aacaggggagagtgt (SEQ ID NO: 10) |
| | D I K M T Q S P S S M Y A S L G E R V T I T C K A S Q D I<br>N S Y L S W F Q Q K P G K S P K T L I Y R A N R L V D G V<br>P S R F S G S G S G Q D F S L T I S S L E Y E D M G I Y Y<br>C L Q Y D E F P Y T F G G G T K L E I K R T V A A P S V F<br>I F P P S D E Q L K S G T A S V V C L L N N F Y P R E A K<br>V Q W K V D N A L Q S G N S Q E S V T E Q D S K D S T Y S<br>L S S T L T L S K A D Y E K H K V Y A C E V T H Q G L S S<br>P V T K S F N R G E C (SEQ ID NO: 11) |
| 3D4rS9-A | Heavy chain |
| | cagatccagttggtgcagtctggacctgagctgaagaagcctggagagacagtcaag<br>atctcctgcaaggcttctgggtataccttcacaaactatggaatgaactgggtgagg<br>caggctccaggaaaggctttaaagtggatggtctggatgaacaccaacactggagag<br>tcaatatatgctgaggagttcaagggacggtttgtcttctctttggatacctctgcc<br>agtactgcctatttgcagatcaacaacctcaacaatgaggacacggctacatattc<br>tgtgcaagatactgggacacctattggggccaaggcaccactctcacagtctcctca<br>gctagcaccaagggcccatcggtcttccccctggcaccctcctccaagagcacctct<br>gggggcacagcggccctgggctgcctggtcaaggactacttccccgaaccggtgacg<br>gtgtcgtggaactcaggcgccctgaccagcggcgtgcacaccttcccggctgtccta<br>cagtcctcaggactctactccctcagcagcgtggtgaccgtgccctccagcagcttg<br>ggcacccagacctacatctgcaacgtgaatcacaagcccagcaacaccaaggtggac<br>aagaaagcagagcccaaatcttgtgacaaaactcacacatgcccaccgtgcccagca<br>cctgaactcctggggggaccgtcagtcttcctcttccccccaaaacccaaggacacc<br>ctcatgatctcccggacccctgaggtcacatgcgtggtggtggacgtgagccacgaa<br>gaccctgaggtcaagttcaactggtacgtggacggcgtggaggtgcataatgccaag<br>acaaaggacgacgacgatgacgataagcctctgggcctggccagacgcggagaaga<br>agaaggcgcagacggaagcacagccctgcctgcgcttttctgccactgggcctggcg<br>ggccgggaggagcagtcaacagcacgtaccgtgtggtcagcgtcctcaccgtcctg<br>caccaggactggctgaatggcaaggactacaagtgcaaggtctccaacaaagccctc<br>ccagcccccatcgagaaaaccatctccaaagccaaagggcagccccgagaaccacag<br>gtgtacaccctgcccccatcccgggatgagctgaccaggaaccaggtcagcctgacc<br>tgcctggtcaaaggcttctatcccagcgacatcgccgtggagtgggagagcaatggg<br>cagccggagaacaactacaagaccacgcctcccgtgctggactccgacggctccttc<br>ttcctctacagcaagctcaccgtggacaagagcaggtggcagcaggggaacgtcttc<br>tcatgctccgtgatgcatgaggctctgcacaaccactacacgcagaagagcctctcc<br>ctgtctccgggtaaa (SEQ ID NO: 18) |
| | Q I Q L V Q S G P E L K K P G E T V K I S C K A S G Y T F<br>T N Y G M N W V R Q A P G K A L K W M V W M N T N T G E S<br>I Y A E E F K G R F V F S L D T S A S T A Y L Q I N N L N<br>N E D T A T Y F C A R Y W D T Y W G Q G T T L T V S S A S<br>T K G P S V F P L A P S S K S T S G G T A A L G C L V K D<br>Y F P E P V T V S W N S G A L T S G V H T F P A V L Q S S<br>G L Y S L S S V V T V P S S S L G T Q T Y I C N V N H K P<br>S N T K V D K K A E P K S C D K T H T C P P C P A P E L L<br>G G P S V F L F P P K P K D T L M I S R T P E V T C V V V<br>D V S H E D P E V K F N W Y V D G V E V H N A K T K <u>D D D</u><br><u>D D D K P L G L A R</u> <u>R R R R R R R R R</u> <u>K H S P A C A F L P</u><br><u>L G L A G</u> R E E Q Y N S T Y R V V S V L T V L H Q D W L N<br>G K D Y K C K V S N K A L P A P I E K T I S K A K G Q P R<br>E P Q V Y T L P P S R D E L T R N Q V S L T C L V K G F Y<br>P S D I A V E W E S N G Q P E N N Y K T T P P V L D S D G<br>S F F L Y S K L T V D K S R W Q Q G N V F S C S V M H E A<br>L H N H Y T Q K S L S L S P G K (SEQ ID NO: 19) |
| | Light chain |
| | Gacatcaagatgacccagtctccatcttccatgtatgcatctctaggagagagtc<br>actatcacttgcaaggcgagtcaggacattaatagctatttaagctggttccagcag |

| Antibody | Nucleic acid sequence and amino acid for heavy and light chain |
|---|---|
| | aaaccagggaaatctcctaagaccctgatctatcgtgcaaacagattggtagatggg<br>gtcccatcaaggttcagtggcagtggatctgggcaagattttctctcaccatcagc<br>agccttgagtatgaagatatgggaatttattattgtctacagtatgatgagtttccg<br>tacacgttcggaggggggaccaagctggaaatcaaacgtacggtggctgcaccatct<br>gtcttcatcttcccgccatctgatgagcagttgaaatctggaactgcctctgttgtg<br>tgcctgctgaataacttctatcccagagaggccaaagtacagtggaaggtggataac<br>gccctccaatcgggtaactcccaggagagtgtcacagagcaggacagcaaggacagc<br>acctacagcctcagcagcaccctaacgctgagcaaagcagactacgagaaacacaaa<br>gtctacgcctgcgaagtcacccatcagggcctgagctcgcccgtcacaaagagcttc<br>aacaggggagagtgt (SEQ ID NO: 10)<br><br>D I K M T Q S P S S M Y A S L G E R V T I T C K A S Q D I<br>N S Y L S W F Q Q K P G K S P K T L I Y R A N R L V D G V<br>P S R F S G S G S G Q D F S L T I S S L E Y E D M G I Y Y<br>C L Q Y D E F P Y T F G G G T K L E I K R T V A A P S V F<br>I F P P S D E Q L K S G T A S V V C L L N N F Y P R E A K<br>V Q W K V D N A L Q S G N S Q E S V T E Q D S K D S T Y S<br>L S S T L T L S K A D Y E K H K V Y A C E V T H Q G L S S<br>P V T K S F N R G E C (SEQ ID NO: 11) |
| 3D4rS9-D | Heavy chain |
| | cagatccagttggtgcagtctggacctgagctgaagaagcctggagagacagtcaag<br>atctcctgcaaggcttctgggtataccttcacaaactatggaatgaactgggtgagg<br>caggctccaggaaaggctttaaagtggatggtctggatgaacaccaacactggagag<br>tcaatatatgctgaggagttcaagggacggtttgtcttctcttggatacctctgcc<br>agtactgcctatttgcagatcaacaacctcaacaatgaggacacggctacatatttc<br>tgtgcaagatactgggacacctattggggccaaggcaccactctcacagtctcctca<br>gctagcaccaagggcccatcggtcttccccctggcaccctcctccaagagcacctct<br>gggggcacagcggccctgggctgcctggtcaaggactacttccccgaaccggtgacg<br>gtgtcgtggaactcaggcgccctgaccagcggcgtgcacaccttcccggctgtccta<br>cagtcctcaggactctactccctcagcagcgtggtgaccgtgccctccagcagcttg<br>ggcacccagacctacatctgcaacgtgaatcacaagcccagcaacaccaaggtggac<br>aagaaagcagagcccaaatcttgtgacaaaactcacacatgcccaccgtgcccagca<br>cctgaactcctgggggaccgtcagtcttcctcttccccccaaaacccaaggacacc<br>ctcatgatctcccggacccctgaggtcacatgcgtggtggtggacgacgacgatgac<br>gataagcctctgggcctggccagacggcggagaagaagaaggcgcagacggaagcac<br>agccctgcctgcgcttttctgccactgggcctggcgggcgtgagccacgaagaccct<br>gaggtcaagttcaactggtacgtggacggcgtggaggtgcataatgccaagacaaag<br>ccgcgggaggagcagtacaacagcacgtaccgtgtggtcagcgtcctcaccgtcctg<br>caccaggactggctgaatggcaaggactacaagtgcaaggtctccaacaaagccctc<br>ccagcccccatcgagaaaaccatctccaaagccaaagggcagccccgagaaccacag<br>gtgtacaccctgcccccatcccgggatgagctgaccaggaaccaggtcagcctgacc<br>tgcctggtcaaaggcttctatcccagcgacatcgccgtggagtgggagagcaatggg<br>cagccggagaacaactacaagaccacgcctcccgtgctggactccgacggctccttc<br>ttcctctacagcaagctcaccgtggacaagagcaggtggcagcaggggaacgtcttc<br>tcatgctccgtgatgcatgaggctctgcacaaccactacacgcagaagagcctctcc<br>ctgtctccgggtaaa (SEQ ID NO: 20)<br><br>Q I Q L V Q S G P E L K K P G E T V K I S C K A S G Y T F<br>T N Y G M N W V R Q A P G K A I K W M V W M N T N T G E S<br>I Y A E E F K G R F V F S L D T S A S T A Y L Q I N N L N<br>N E D T A Y Y F C A R Y W D T Y W G Q G T T L T V S S A S<br>T K G P S V F P L A P S S K S T S G G T A A L G C L V K D<br>Y F P E P V T V S W N S G A L T S G V H T F P A V L Q S S<br>G L Y S L S S V V T V P S S S L G T Q T Y I C N V N H K P<br>S N T K V D K K A E P K S C D K T H T C P P C P A P E L L<br>G G P S V F L P P K P K D T L M I S R T P E V T C V V V<br><u>D D D D D D K P L G L A R R R R R R R R R</u> K H S P A C A<br><br><u>F L P L G L A G</u> V S H E D P E V K F N W Y V D G V E V H N<br>A K T K P R E E Q Y N S T Y R V V S V L T V L H Q D W L N<br>G K D Y K C K V S N K A L P A P I E K T I S K A K G Q P R<br>E P Q V Y T L P P S R D E L T R N Q V S L T C L V K G F Y<br>P S D I A V E W E S N G Q P E N N Y K T T P P V L D S D G<br>S F F L Y S K L T V D K S R W Q Q G N V F S C S V M H S A<br>L H N H Y T Q K S L S L S P G K (SEQ ID NO: 21) |
| | Light chain |
| | Gacatcaagatgacccagtctccatcttccatgtatgcatctctaggagagagagtc<br>actatcacttgcaaggcgagtcaggacattaatagctatttaagctggttccagcag<br>aaaccagggaaatctcctaagaccctgatctatcgtgcaaacagattggtagatggg<br>gtcccatcaaggttcagtggcagtggatctgggcaagattttctctcaccatcagc<br>agccttgagtatgaagatatgggaatttattattgtctacagtatgatgagtttccg<br>tacacgttcggaggggggaccaagctggaaatcaaacgtacggtggctgcaccatct<br>gtcttcatcttcccgccatctgatgagcagttgaaatctggaactgcctctgttgtg |

| Antibody | Nucleic acid sequence and amino acid for heavy and light chain |
|---|---|
| | tgcctgctgaataacttctatcccagagaggccaaagtacagtggaaggtggataac<br>gccctccaatcgggtaactcccaggagagtgtcacagagcaggacagcaaggacagc<br>acctacagcctcagcagcacccctaacgctgagcaaagcagactacgagaaacacaaa<br>gtctacgcctgcgaagtcacccatcagggcctgagctcgcccgtcacaaagagcttc<br>aacaggggagagtgt (SEQ ID NO: 10)<br><br>D I K M T Q S P S S M Y A S L G E R V T I T C K A S Q D I<br>N S Y L S W F Q Q K P G K S P K T L I Y R A N R L V D G V<br>P S R F S G S G S G Q D F S L T I S S L E Y E D M G I Y Y<br>C L Q Y D E F P Y T F G G G T K L E I K R T V A A P S V F<br>I F P P S D E Q L K S G T A S V V C L L N N F Y P R E A K<br>V Q W K V D N A L Q S G N S Q E S V T E Q D S K D S T Y S<br>L S S T L T L S K A D Y E K H K V Y A C E V T H Q G L S S<br>P V T K S F N R G E C (SEQ ID NO: 11) |
| 3D4Fc-rS9 | Heavy chain |
| | cagatccagttggtgcagtctggacctgagctgaagaagcctggagagacagtcaag<br>atctcctgcaaggcttctgggtataccttcacaaactatggaatgaactgggtgagg<br>caggctccaggaaaggctttaaagtggatggtctggataacaccaacactggagag<br>tcaatatatgctgaggagttcaaaggacggtttgtcttctctttggatacctctgcc<br>agtactgcctatttgcagatcaacaacctcaacaatgaggacacggctacatatttc<br>tgtgcaagatactgggacacctattggggccaaggcaccactctcacagtctcctca<br>gctagcaccaagggcccatcggtcttcccctggcaccctcctccaagagcacctct<br>gggggcacagcggccctgggctgcctggtcaaggactacttccccgaaccggtgacg<br>gtgtcgtggaactcaggcgccctgaccagcggcgtgcacaccttcccggctgtccta<br>cagtcctcaggactctactccctcagcagcgtggtgaccgtgccctccagcagcttg<br>ggcacccagacctacatctgcaacgtgaatcacaagcccagcaacaccaaggtggac<br>aagaaagcagagcccaaatcttgtgacaaaactcacacatgcccaccgtgcccagca<br>cctgaactcctggggggaccgtcagtcttcctcttccccccaaaacccaaggacacc<br>ctcatgatctcccggacccctgaggtcacatgcgtggtggtggacgtgagccacgaa<br>gaccctgaggtcaagttcaactggtacgtggacggcgtggaggtgcataatgccaag<br>acaaagccgcgggaggagcagtacaacagcacgtaccgtgtggtcagcgtcctcacc<br>gtcctgcaccaggactggctgaatggcaaggactacaagtgcaaggtctccaacaaa<br>gccctcccagcccccatcgagaaaaccatctccaaagccaaagggcagccccgagaa<br>ccacaggtgtacaccctgcccccatcccgggatgagctgaccaggaaccaggtcagc<br>ctgacctgcctggtcaaaggcttctatcccagcgacatcgccgtggagtgggagagc<br>aatgggcagccggagaacaactacaagaccacgcctcccgtgctggactccgacggc<br>tccttcttcctctacagcaagctcaccgtggacaagagcaggtggcagcaggggaac<br>gtcttctcatgctccgtgatgcatgaggctctgcacaaccactacacgcagaagagc<br>ctctccctgtctccgggtaaagacgacgacgatgacgataagcctctgggcctggcc<br>ggacggcggaagaagaaggcgcagacggaagcacagccctgcctgcgcttttctg<br>(SEQ ID NO: 22)<br><br>Q I Q L V Q S G P E L K K P G E T V K I S C K A S G Y T F<br>T N Y G M N W V R Q A P G K A L K W M V W M N T N T G E S<br>I Y A E E F K G R F V F S L D T S A S T A Y L Q I N N L N<br>N E D T A T Y F C A R Y W D T Y W G Q G T T L T V S S A S<br>T K G P S V F P L A P S S K S T S G G T A A L G C L V K D<br>Y F P E P V T V S W N S G A L T S G V H T F P A V L Q S S<br>G L Y S L S S V V T V P S S S L G T Q T Y I C N V N H K P<br>S N T K V D K K A E P K S C D K T K T C P P C P A P E L L<br>G G P S V F L F P P K P K D T L M I S R T P E V T C V V V<br>D V S H E D P E V K F N W Y V D G V E V H N A K T K P R E<br>E Q Y N S T Y R V V S V L T V L H Q D W L N G K D Y K C K<br>V S N K A L P A P I E K T I S K A K G Q P R E P Q V Y T L<br>P P S R D E L T R N Q V S L T C L V K G F Y P S D I A V E<br>W E S N G Q P E N N Y K T T P P V L D S D G S F F L Y S K<br>L T V D K S R W Q Q G N V F S C S V M H E A L H N H Y T Q<br>K S L S L S P G K <u>D D D D D D K P L G L A G R R R R R R</u><br><u>R R</u> K H S P A C A F L<br>(SEQ ID NO: 23) |
| | Light chain |
| | Gacatcaagatgacccagtctccatcttccatgtatgcatctctaggagagagagtc<br>actatcacttgcaaggcgagtcaggacattaatagctatttaagctggttccagcag<br>aaaccagggaaatcctaagaccctgatctatcgtgcaaacagattggtagatggg<br>gtcccatcaaggttcagtggcagtggatctgggcaagattttctctcaccatcagc<br>agccttgagtatgaagatatgggaatttattattgtctacagtatgatgagtttccg<br>tacacgttcggaggggggaccaagctggaaatcaaacgtacggtggctgcaccatct<br>gtcttcatcttcccgccatctgatgagcagttgaaatctggaactgcctctgttgtg<br>tgcctgctgaataacttctatcccagagaggccaaagtacagtggaaggtggataac<br>gccctccaatcgggtaactcccaggagagtgtcacagagcaggacagcaaggacagc |

| Antibody | Nucleic acid sequence and amino acid for heavy and light chain |
|---|---|
| | acctacagcctcagcagcaccctaacgctgagcaaagcagactacgagaaacacaaa<br>gtctacgcctgcgaagtcacccatcagggcctgagctcgcccgtcacaaagagcttc<br>aacaggggagagtgt (SEQ ID NO: 10)<br><br>D I K M T Q S P S S M Y A S L G E R V T I T C K A S Q D I<br>N S Y L S W F Q Q K P G K S P K T L I Y R A N R L V D G V<br>P S R F S G S G S G Q D F S L T I S S L E Y E D M G I Y Y<br>C L Q Y D E F P Y T F G G G T K L E I K R T V A A P S V F<br>I F P P S D E Q L K S G T A S V V C L L N N F Y P R E A K<br>V Q W K V D N A L Q S G N S Q E S V T E Q D S K D S T Y S<br>L S S T L T L S K A D Y E K H K V Y A C E V T H Q G L S S<br>P V T K S F N R G E C (SEQ ID NO: 11) |

In the table, the amino acids marked with underline is the acidic domain (PAD);
the amino acids marked with dash underline is the cleavage linker (CL);
the amino acids marked with double underline is the basic domain (PCD);
and the amino acids marked with dot underline is the effector peptide (EP).

The preparation of the fusion protein may be performed by any general method for preparing a protein, such as a chemical synthesis of a protein, a protein expression using an expression (recombinant) vector comprising (carrying) polynucleotides encoding each component of the fusion protein (in a proper host cell), and the like.

The fusion protein of the invention can be manufactured according to the conventional publicly-known gene engineering technique. Thus, for example, each of DNA encoding the Ab and DNAs encoding the CPEP is amplified if necessary, those DNAs are bound each other, the resulting DNA is inserted into a cellular expression vector and a host cell is to transfected with the vector to express the fusion protein whereby fusion protein of the invention can be manufactured. Amplification of DNA can be conducted by, for example, a PCR method. Binding of the amplified DNA can be conducted, for example, by an overlap extension PCR method. It is also possible to design an amino acid sequence of fusion protein to be expressed so as to directly prepare an artificial synthetic gene. It is preferred that the expression vector includes a promoter for enhancing the expression efficiency and a secretion signal sequence such as antibody heavy chain signal sequence or antibody kappa chain signal sequence for easy recovery of the expressed fusion protein from culture supernatant. As to the expression host cell, mammalian cell, yeast, animal cell, insect cell, plant cell, bacterial cell (*Escherichia coli* etc.) etc. can be used. Among them, animal cell is preferred and CHO cell, HEK293 cell, etc. are particularly preferred.

For a person skilled in the art it will be apparent that the fusion protein thus defined can be synthesized by known methods of chemical synthesis of peptides and proteins. The fusion protein can be synthesized by methods of chemical peptide synthesis, especially using the techniques of peptide synthesis in solid phase using suitable resins as carriers. Alternatively, the fusion protein can be synthesized by the methods of chemical synthesis of peptides as a continuous protein. Alternatively, the individual fragments (domains) of protein may be synthesized separately and then combined together in one continuous peptide via a peptide bond, by condensation of the amino terminus of one peptide fragment from the carboxyl terminus of the second peptide. Such techniques are conventional and well known.

The present invention also provides compositions for use in delivery of an effector peptide into a cell. In one embodiment, the composition comprises the fusion protein of the invention and a pharmacologically suitable carrier. Typically, such compositions are prepared either as liquid solutions or suspensions, however solid forms such as tablets, pills, powders and the like are also contemplated. The fusion protein of the invention may be mixed with excipients which are pharmaceutically acceptable and compatible with the fusion protein. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain various adjuvants (compounds that can induce or increase the humoral and/or cellular immune response towards an antigen or immunogen). If it is desired to administer an oral form of the composition, various thickeners, flavorings, diluents, emulsifiers, dispersing aids or binders and the like may be added. The composition of the invention may contain any such additional ingredients so as to provide the composition in a form suitable for administration.

The compositions (preparations, formulations, etc.) of the invention may be administered by any of the many suitable means which are well known to those of skill in the art, including but not limited to by parenteral (including, for example, intraarterial, intravenous, intramuscular, subcutaneous), topical (including dermal, transdermal, subcutaneous, etc), oral, nasal, mucosal (including sublingual) and intracavitary routes (such as intravaginal, intracervical, intrauterine, intrapenis and intranasal). In some embodiments, the mode of administration is by injection, intradermally or orally.

The invention also provides methods for delivering an effector peptide into a cell and/or a cell nucleus, comprising administering a fusion protein of the invention or a composition comprising the fusion protein of the invention to a subject. Accordingly, the invention provides a use of a fusion protein of the invention in the manufacture of a medicament for delivering an effector peptide into a cell and/or a cell nucleus. The fusion protein of the invention can be administered for cancers, fibrosis, inflammation diseases, metabolic disorders, immune system disorders, infectious diseases, anti-aging and enzyme replacement therapies depending on the effector peptide to be delivered by the fusion protein. The fusion protein can achieve intra-cellular and intra-nucleus drug delivery. The forgoing examples serve to further illustrate particular embodiments of the invention but should not be interpreted as limiting the invention in any way.

EXAMPLES

Figure 1:
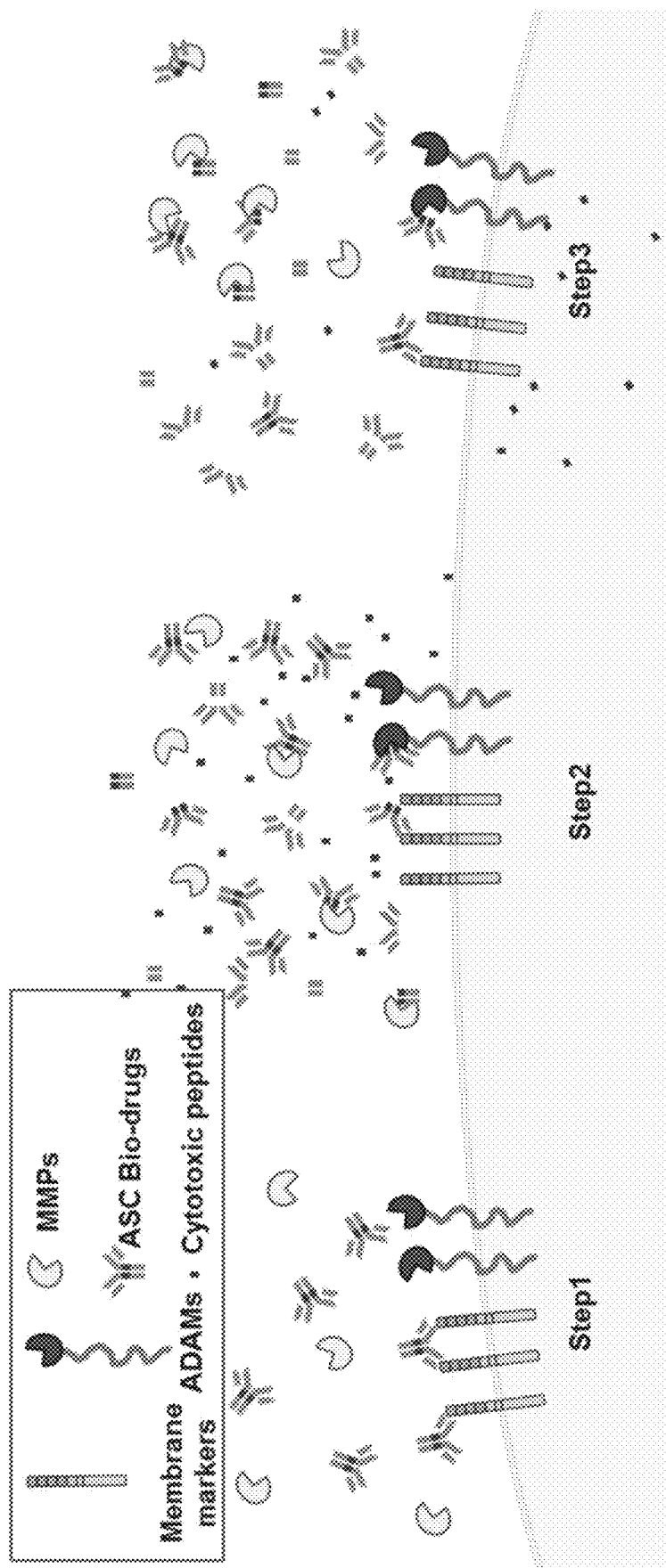

Example 1 Mechanism of Action of the Bio-Drugs Delivery Technology of the Invention A schematic diagram of the mechanism of action (MOA) of this innovative bio-drugs delivery technology for cancer treatment, the ASC (Antibody Switched-on Cytotoxicity) biologics platform, which utilizes antibodies targeting to cell surface (Step 1); and then the CPEP are activated in the tumor microenvironment (step2) and the CPP (cell penetrating peptide)/PCD deliver the EP which are cytotoxic peptide payloads into cells (step3) display in FIG. 1.

Example 2 ASC Bio Drugs Expression and Purification

The genes for each ASC bio drugs were de novo DNA synthesis or PCR-based synthesis, and were cloned into the modified mammalian expression vector. The ASC bio drugs (3D4scr, 3D4KLA, 3D4S9, 3D4rS9, 3D4rS9-ΔD6, 3D4rS9-A, 3D4S9-D and 3D4Fc-rS9) are produced based on anti-DSG2 antibody (3D4). 3D4scr having the EP without cytotoxicity was also produced based on anti-DSG2 antibody (3D4) as positive control. The nucleotide and amino acid sequences of 3D4 and 3D4scr are listed in Table 1 below. The nucleotide and amino acid sequences of each ASC bio drugs are described in previous sequence table (see paragraph [0071]). The ASC bio drugs were expressed by transient gene expression with the Expi293™ Expression System (Thermo Fisher Scientific) following the manufacturer's instructions. ASC bio drugs were purified from Expi293™ supernatants by protein A affinity purification (GE Healthcare). After the protein A resins were washed with 0.1 M Tris, pH 8.0 and 10 mM Tris, pH8.0, the ASC bio drugs were eluted with 0.1 M glycin, pH 3.0, followed by the rapid adjustment of sample pH with the addition of 0.1 mL of 1 M Tris-HCl, pH 8.0 per 1 mL eluate. Protein solutions were then buffer exchanged with PBS using a PD-10 (Nap-10) Desalting Column (GE Healthcare) and finally concentrated using a Vivaspin Protein Concentrator Spin Column (GE Healthcare). The resulting ASC bio drugs include 3D4scr, 3D4KLA, 3D4S9, 3D4rS9, 3D4rS9-ΔD6, 3D4rS9-A, 3D4S9-D and 3D4Fc-rS9.

TABLE 1

| Antibody | Nucleic acid sequence and amino acid for heavy and light chain |
|---|---|
| 3D4 | Heavy Chain |
| (anti-DSG2) | Q I Q L V Q S G P E L K K P G E T V K I S C K A S G Y T F<br>T N Y G M N W V R Q A P G K A L K W M V W M N T N T G E S<br>I Y A E E F K G R F V F S L D T S A S T A Y L Q I N N L N<br>N E D T A T Y F C A R Y W D T Y W G Q G T T L T V S S A S<br>T K G P S V F P L A P S S K S T S G G T A A L G C L V K D<br>Y F P E P V T V S W N S G A L T S G V H T F P A V L Q S S<br>G L Y S L S S V V T V P S S S L G T Q T Y I C N V N H K P<br>S N T K V D K K A E P K S C D K T H T C P P C P A P E L L<br>G G P S V F L F P P K P K D T L M I S R T P E V T C V V V<br>D V S H E D P E V K F N W Y V D G V E V H N A K T K P R E<br>E Q Y N S T Y R V V S V L T V L H Q D W L N G K D Y K C K<br>V S N K A L P A P I E K T I S K A K G Q P R E P Q V Y T L<br>P P S R D E L T R N Q V S L T C L V K G F Y P S D I A V E<br>W E S N G Q P E N N Y K T T P P V L D S D G S F F L Y S K<br>L T V D K S R W Q Q G N V F S C S V M H E A L H N H Y T Q<br>K S L S L S P G K (SEQ ID NO: 24) |
| | Light chain |
| | D I K M T Q S P S S M Y A S L G E R V T I T C K A S Q D I<br>N S Y L S W F Q Q K P G K S P K T L I Y R A N R L V D G V<br>P S R F S G S G S G Q D F S L T I S S L E Y E D M G I Y Y<br>C L Q Y D E F P Y T F G G G T K L E I K R T V A A P S V F<br>I F P P S D E Q L K S G T A S V V C L L N N F Y P R E A K<br>V Q W K V D N A L Q S G N S Q E S V T E Q D S K D S T Y S<br>L S S T L T L S K A D Y E K H K V Y A C E V T H Q G L S S<br>P V T K S F N R G E C (SEQ ID NO: 11) |
| 3D4scr | Heavy chain |
| | cagatccagttggtgcagtctggacctgagctgaagaagcctggagagacagtcaag<br>atctcctgcaaggcttctgggtataccttcacaaactatggaatgaactgggtgagg<br>caggctccaggaaaggctttaaagtggatggtctggatgaacaccaacactggagag<br>tcaatatatgctgaggagttcaagggacggtttgtcttctctttggatacctctgcc<br>agtactgcctatttgcacatcaacaacctcaacaatgaggacacggctacatatttc<br>tgtgcaagatactgggacacctattggggccaaggcaccactctcacagtctcctca<br>gctagcaccaagggcccatcggtcttccccctggcaccctcctccaagagcacctct<br>gggggcacagcggccctgggctgcctggtcaaggactacttccccgaaccggtgacg<br>gtgtcgtggaactcaggcgccctgaccagcggcgtgcacaccttcccggctgtccta<br>cagtcctcaggactctactccctcagcagcgtggtgaccgtgccctccagcagcttg<br>ggcacccagacctacatctgcaacgtgaatcacaagcccagcaacaccaaggtggac<br>aagaaagcagagcccaaatcttgtgacaaaactcacacatgcccaccgtgcccagat<br>aacgacgatgatgacaaaccactgggcctggccagacgccggagaaggagacgcagg<br>cggagactgcattgcaaatcctttgcaagcggcccactgggcctggcgggcgcacct<br>gaactcctgggggaccgtcagtcttcctcttccccccaaaacccaaggacaccctc<br>atgatctcccggacccctgaggtcacatgcgtggtggtggacgtgagccacgaagac<br>cctgaggtcaagttcaactggtacgtggacggcgtggaggtgcataatgccaagaca<br>aagccgcgggaggagcagtacaacagcacgtaccgtgtggtcagcgtcctcaccgtc |

TABLE 1-continued

| Antibody | Nucleic acid sequence and amino acid for heavy and light chain |
|---|---|

```
ctgcaccaggactggctgaatggcaaggactacaagtgcaaggtctccaacaaagcc
ctcccagccccatcgagaaaaccatctccaaagccaaagggcagccccgagaacca
caggtgtacaccctgccccatcccgggatgagctgaccaggaaccaggtcagcctg
acctgcctggtcaaaggcttctatcccagcgacatcgccgtggagtgggagagcaat
gggcagccggagaacaactacaagaccacgcctcccgtgctggactccgacggctcc
ttcttcctctacagcaagctcaccgtggacaagagcaggtggcagcaggggaacgtc
ttctcatgctccgtgatgcatgaggctctgcacaaccactacacgcagaagagcctc
tccctgtctccgggtaaa (SEQ ID NO: 25)
```

```
Q I Q L V Q S G P E L K K P G E T V K I S C K A S G Y T F
T N Y G M N W V R Q A P G K A L K W M V W M N T N T G E S
I Y A E E F K G R F V F S L D T S A S T A Y L Q I N N L N
N E D T A T Y F C A R Y W D T Y W G Q G T T L T V S S A S
T K G P S V F P L A P S S K S T S G G T A A L G C L V K D
Y F P E P V T V S W N S G A L T S G V H T F P A V L Q S S
G L Y S L S S V V T V P S S S L G T Q T Y I C N V N H K P
S N T K V D K K A E P K S C D K T H T C P P C P D D D D D
D K P L G L A R R R R R R R R R L H C K S F A S G P L G
L A G A P E L L G G P S V F L F P P K P K D T L M I S R T
P E V T C V V V D V S H E D P E V K F N W Y V D G V E V H
N A K T K P R E E Q Y N S T Y R V V S V L T V L H Q D W L
N G K D Y K C K V S N K A L P A P I E K T I S K A K G Q P
R E P Q V Y T L P P S R D E L T R N Q V S L T C L V K G F
Y P S D I A V E W E S N G Q P E N N Y K T T P P V L D S D
G S F F L Y S K L T V D K S R W Q Q G N V F S C S V M H E
A L H N H Y T Q K S L S L S P G K (SEQ ID NO: 26)
```

Light chain

```
Gacatcaagatgacccagtctccatcttccatgtatgcatctctaggagagagagtc
actatcacttgcaaggcgagtcaggacattaatagctatttaagctggttccagcag
aaaccagggaaatctcctaagaccctgatctatcgtgcaaacagattggtagatggg
gtcccatcaaggttcagtggcagtggatctgggcaagattttctctcaccatcagc
agccttgagtatgaagatatgggaatttattattgtctacagtatgatgagtttccg
tacacgttcggagggggggaccaagctggaaatcaaacgtacggtggctgcaccatct
gtcttcatcttcccgccatctgatgagcagttgaaatctggaactgcctctgttgtg
tgcctgctgaataacttctatcccagagaggccaaagtacagtggaaggtggataac
gccctccaatcgggtaactcccaggagagtgtcacagagcaggacagcaaggacagc
acctacagcctcagcagcaccctaacgctgagcaaagcagactacgagaaacacaaa
gtctacgcctgcgaagtcacccatcagggcctgagctcgcccgtcacaaagagcttc
aacaggggagagtgt (SEQ ID NO: 10)
```

```
D I K M T Q S P S S M Y A S L G E R V T I T C K A S Q D I
N S Y L S W F Q Q K P G K S P K T L I Y R A N R L V D G V
P S R F S G S G S G Q D F S L T I S S L E Y E D M G I Y Y
C L Q Y D E F P Y T F G G G T K L E I K R T V A A P S V F
I F P P S D E Q L K S G T A S V V C L L N N F Y P R E A K
V Q W K V D N A L Q S G N S Q E S V T E Q D S K D S T Y S
L S S T L T L S K A D Y E K H K V Y A C E V T H Q G L S S
P V T K S F N R G E C (SEQ ID NO: 11)
```

In the table, the amino acids marked with underline is the acidic domain (PAD);
the amino acids marked with dash underline is the cleavage linker (CL);
the amino acids marked with double underline is the basic domain underline (PCD);
and the amino acids marked with dot underline is the effector peptide (EP).

Example 3 ASC Bio Drugs Analysis by Flow Cytometry

Figure 2:
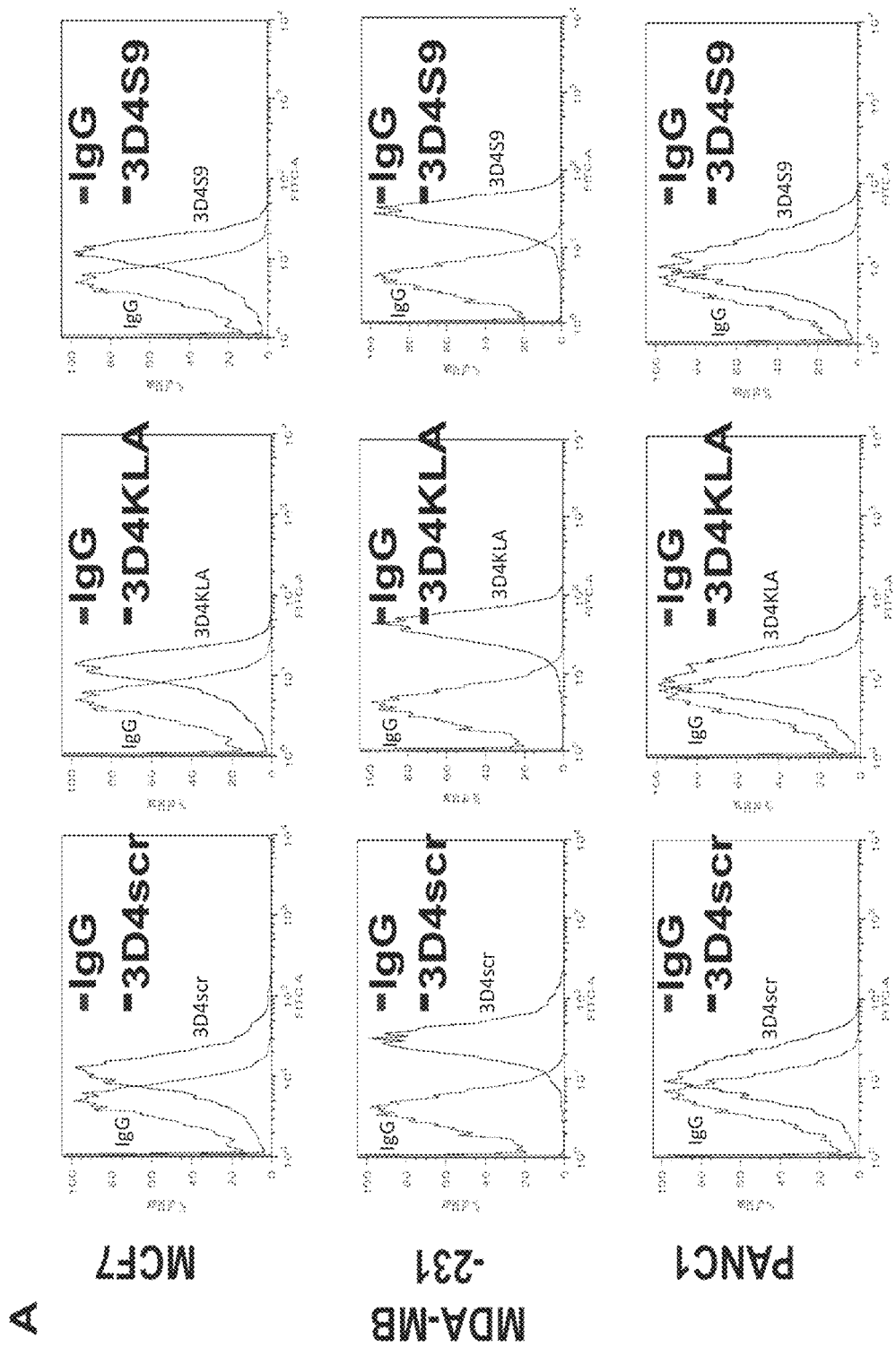
Figure 2:
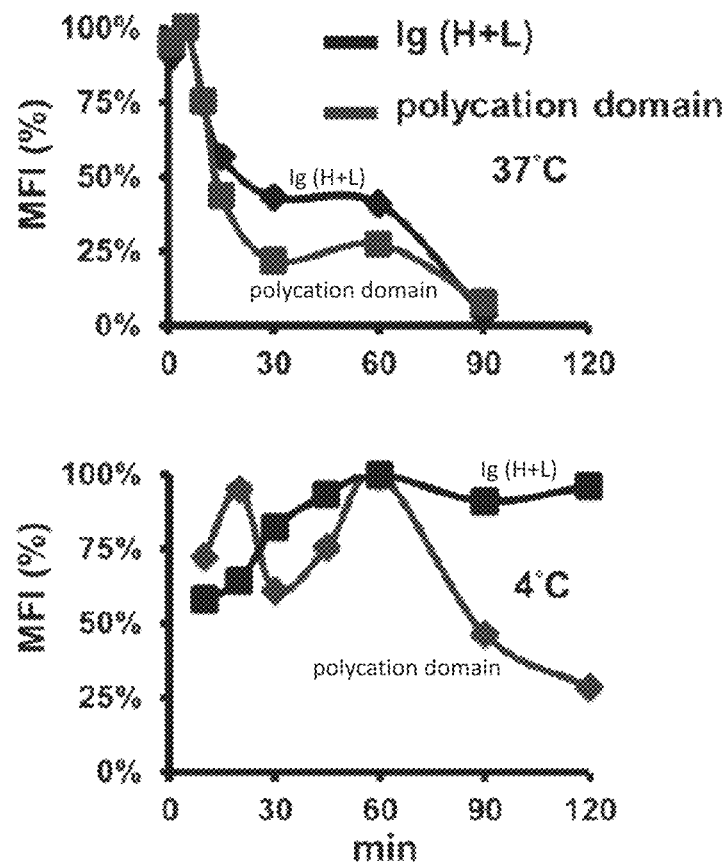
Figure 2:
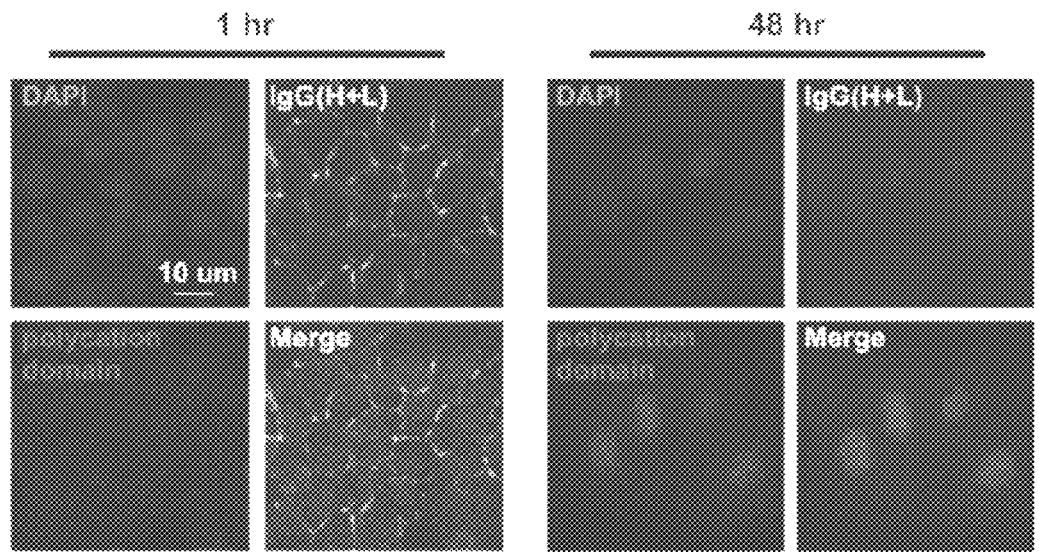
Figure 3:
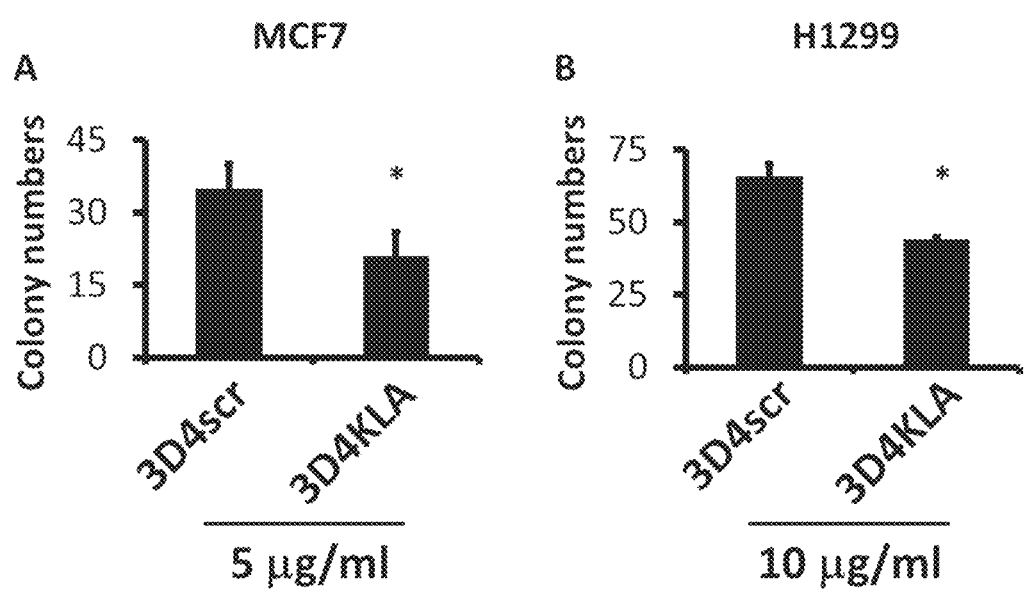
Figure 4:
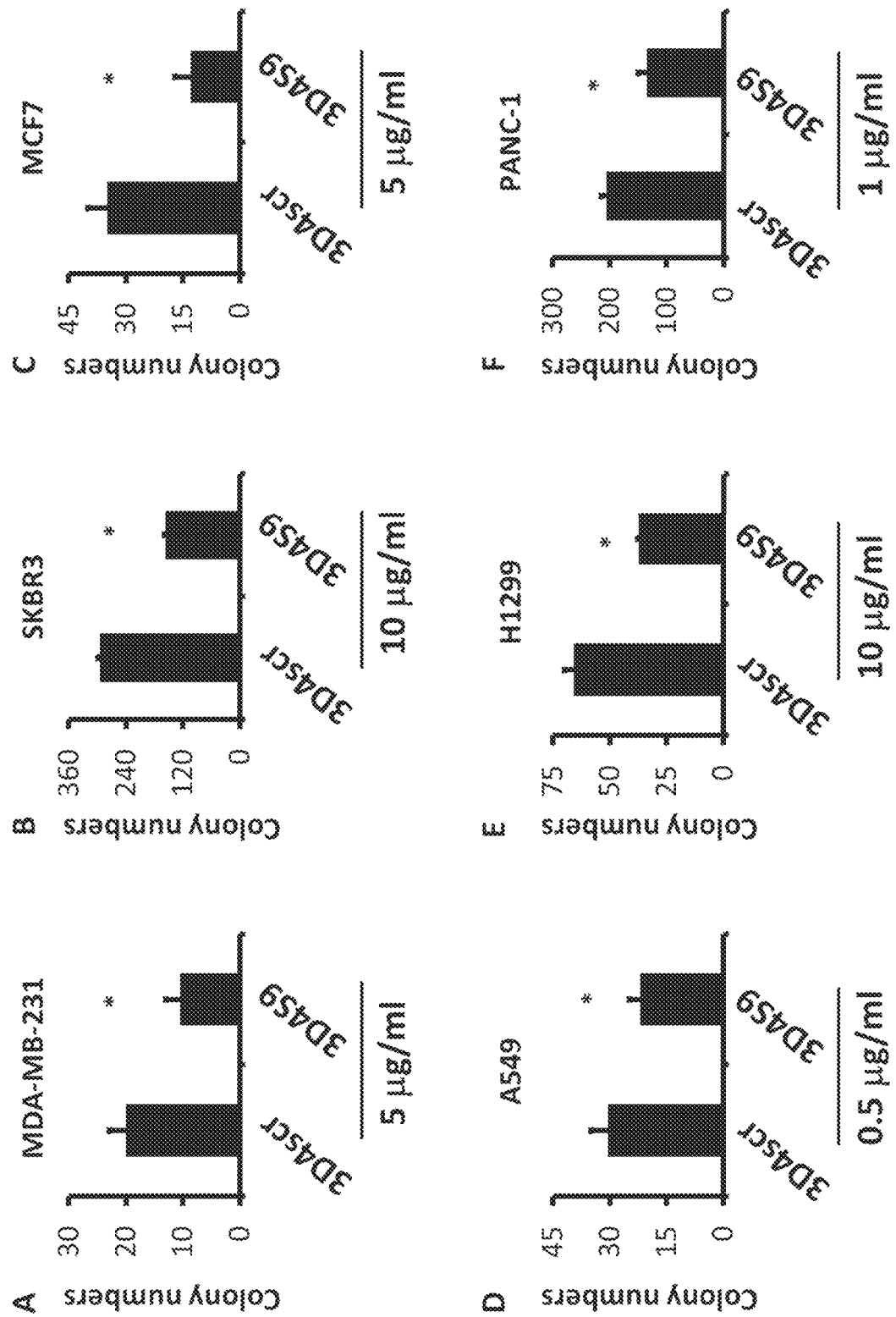
Figure 5:
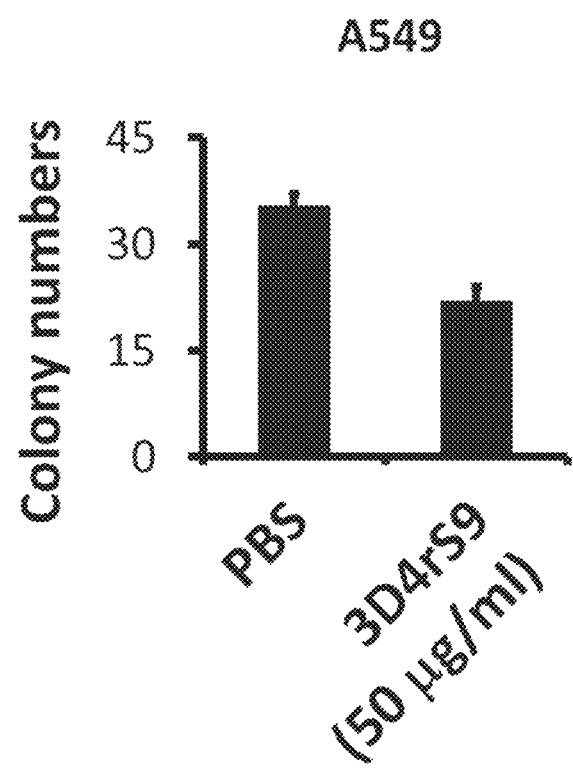

Cells (1×10⁶/ml) were collected and resuspended in PBS with 2% FBS containing 2 mM EDTA, and incubated with 1 g/ml IgG, 3D4scr, 3D4KLA or 3D4S9 for 30 min at 4 C. Cells were washed with PBS twice and then with addition of the secondary FITC-conjugated antibody (Alexa Fluor 488 goat anti-human IgG) for 30 min at 4 C. The samples were washed with PBS twice, and analyzed using flow cytometry. 10000 cellular events were analyzed per sample. FIG. 2 A shows the surface binding ASC bio drugs by flow cytometry and the results show that ASC bio-drugs recognize target cells.

Human breast adenocarcinoma MCF7 cells were collected and resuspended in PBS with 2% FBS containing 2 mM EDTA, and incubated with 3D4S9 (1 μg/ml) for each time point (1, 5, 10, 15, 30, 60, 90 and 120 min) at 4 C or 37 C. All cells were fixed in 1% paraformaldehyde for 10 min, washed with PBS twice, and stained with the primary rabbit anti-linker-X antibodies. Alexa Fluor 594 goat anti-rabbit IgG and Alexa Fluor 488 goat anti-human IgG were used to detect the linker-X and ASC bio drugs, respectively. The samples were analyzed using flow cytometry. 10000 cellular events were analyzed per sample. FIG. 2 B evaluates the cleaved ASC bio drugs by flow cytometry.

Figure 7:
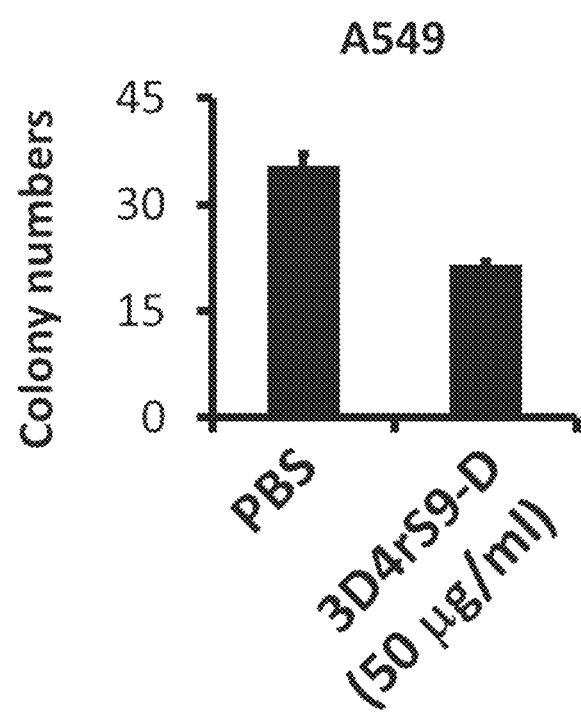
FIG. 7 shows that 3D4rS9-D reduces the transformation activity in the human lung carcinoma A549 cells. Decreased soft agar colony formation activity in human lung carcinoma A549 cells treated with 3D4rS9-D.
Figure 8:
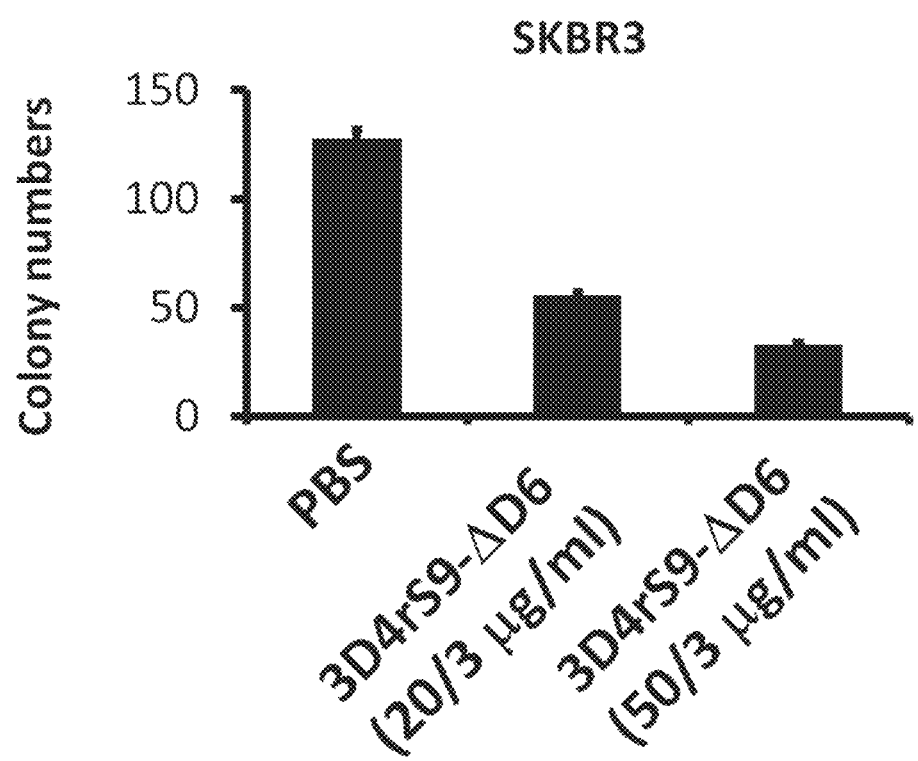
FIG. 8 shows that 3D4rS9-ΔD6 reduces the transformation activity in the human breast adenocarcinoma SKBR3 cells. Decreased soft agar colony formation activity in human breast adenocarcinoma SKBR3 cells treated with 3D4rS9-ΔD6.
Figure 9:
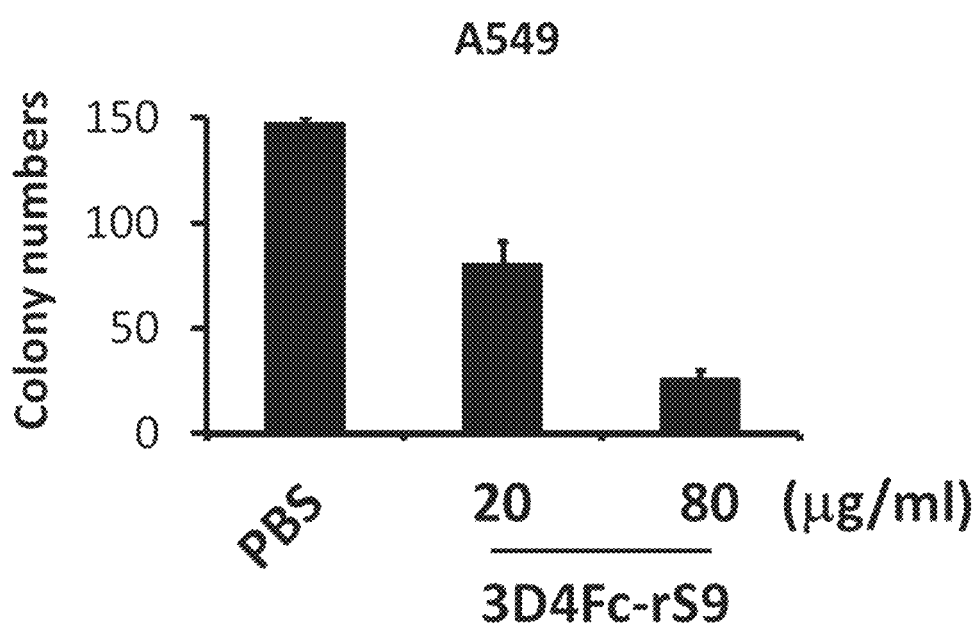
FIG. 9 shows that 3D4Fc-rS9 reduces the transformation activity in the human lung carcinoma A549 cells. Decreased soft agar colony formation activity in human lung carcinoma A549 cells treated with 3D4Fc-rS9.

Human breast adenocarcinoma MCF7 cells were seeded on glass coverslips for 48 hr, and treated with 3D4S9 for 1 and 48 hr at 37° C. Cells on the coverslips were washed with PBS, fixed in 4% paraformaldehyde, washed twice with PBS, and permeabilized with 0.2% Triton X-100 for 15 min. After washing with PBS, cells were blocked with 10% FBS for 1 hr, followed by incubation with the rabbit anti-linker-X antibody. Alexa Fluor 594 goat anti-rabbit IgG and Alexa Fluor 488 goat anti-human IgG were used to visualize the location of Linker-X and ASC bio drugs, respectively. Finally, the fixed cells were washed three times with PBS, and their nuclei were counterstained, mounted, and observed by using fluorescence microscope or confocal microscope. FIG. 2 C shows that fluorescent ICC staining. The results of decreased soft agar colony formation activity in human lung carcinoma A549 cells treated with 3D4rS9-D (FIG. 7); decreased soft agar colony formation activity in human breast adenocarcinoma SKBR3 cells treated with 3D4rS9-ΔD6 (FIG. 8); decreased soft agar colony formation activity in human lung carcinoma A549 cells treated with 3D4Fc-rS9 (FIG. 9)

3D4sc, 3D4S9, 3D4KLA, 3D4rS9, 3D4rS9-ΔD6, 3D4rS9-A, 3D4rS9-D and 3D4Fc-rS9 were used in in vitro inhibition assay in various cancer cell lines and the results are shown in the Table 2 below.

|  |  | ASC bio drug Name | | | | | | | |
|---|---|---|---|---|---|---|---|---|---|
| Disease | Cell line | 3D4scr | 3D4KLA | 3D4S9 | 3D4rS9 | 3D4rS9-ΔD6 | 3D4rS9-A | 3D4rS9-D | 3D4Fc-rS9 |
| Human breast adenocarcinoma | MDA-MB-231 | (−) | ND | (+) | ND | ND | ND | ND | ND |
|  | MCF7 | (−) | (+) | (+) | ND | ND | ND | ND | ND |
|  | SKBR3 | (−) | ND | (+) | ND | (+) | (+) | ND | ND |
| Human lung carcinoma | A549 | (−) | ND | (+) | (+) | ND | (+) | (+) | (+) |
| Human non-small cell lung carcinoma | H1299 | (−) | (+) | (+) | ND | ND | ND | ND | ND |
| Human pancreatic carcinoma | PANC-1 | (−) | ND | (+) | ND | ND | ND | ND | ND |

(−): Negative results, colony formation was not reduced;
(+): Positive results, colony formation was reduced significantly;
ND: (NONE DONE)

FIGS. 2 B and C show that the polycation domain of 3D4S9 is cleaved and internalized into the human breast adenocarcinoma MCF7 cells.

Example 4 Soft Agar Colony Formation Assay

Figure 6:
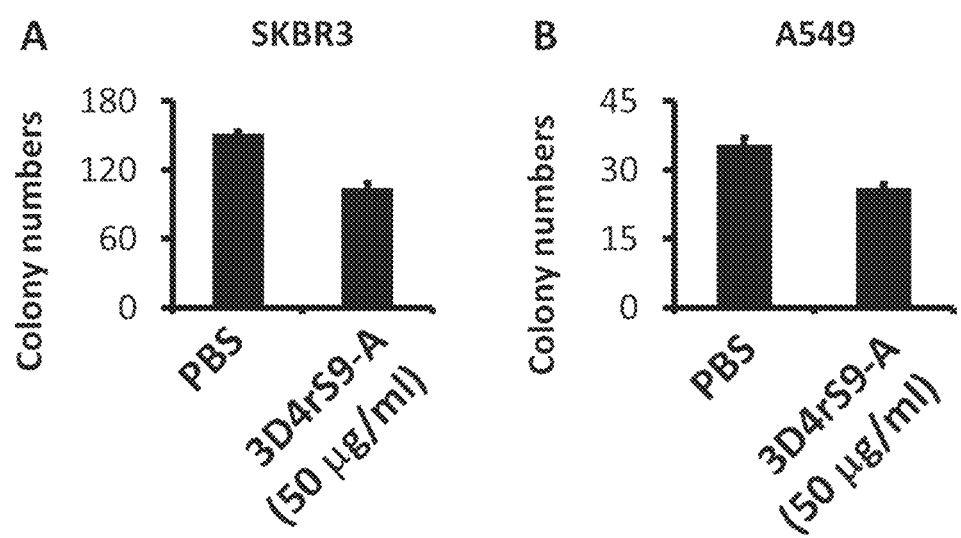

Cells (2×10$^3$) were treated with 3D4scr, 3D4KLA, 3D4S9, 3D4rS9, 3D4rS9-ΔD6, 3D4rS9-A, 3D4S9-D or 3D4Fc-rS9 for 10 mins and then mixed with 0.35% agarose in growth medium, plated on top of a solidified layer of 0.5% agarose in growth medium, in a 12-well plate. After 1-2 weeks, the colonies were dyed with Cristal Violet (0.01% solution) and washed with PBS, and colonies were counted using a microscope. The results of the soft agar colony formation assay of 3D4scr, 3D4KLA, 3D4S9, 3D4rS9, 3D4rS9-ΔD6, 3D4rS9-A, 3D4S9-D or 3D4Fc-rS9 are shown in FIGS. 3 to 9. The results show decreased soft agar colony formation activity in human breast adenocarcinoma MCF7 cells (A) and human non-small cell lung carcinoma H1299 (B) treated with 3D4KLA (FIG. 3); decreased soft agar colony formation activity in human breast adenocarcinoma MDA-MB-231(A), human breast adenocarcinoma SKBR3 (B), human breast adenocarcinoma MCF7 (C), human lung carcinoma A549 (D), human non-small cell lung carcinoma H1299 (E) and human pancreatic adenocarcinoma PANC-1 cells (F) treated with 3D4S9 (FIG. 4); decreased soft agar colony formation activity in human lung carcinoma A549 cells treated with 3D4rS9 (FIG. 5); decreased soft agar colony formation activity in human breast adenocarcinoma SKBR3 (A) and human lung carcinoma A549 cells (B) treated with 3D4rS9-A (FIG. 6);

Example 5 Tumor Xenografts

Six-week-old male non-obese diabetic-severe combined immunodeficiency mice received subcutaneously injection of 2×10$^6$ cells of human pancreatic carcinoma PANC1 cell lines in 0.1 ml of PBS, mixed with Matrigel (1: I). When tumor volume reached around 20 mm$^3$, mice were randomly assigned to each treatment group. 3D4scr and 3D4S9 (30 mg/kg), diluted to with PBS, were intraperitoneally injected, twice-weekly for 3 weeks. Body weight was recorded at the end of the treatment period to evaluate the systematic toxicity of 3D4scr and 3D4S9 therapy. The tumor size was measured with calipers and the tumor volume was calculated according to the formula (length×width$^2$)/2.

FIGS. 10 A to C show that 3D4S9 reduces xenograft tumor growth in NOD/SCID mice using human pancreatic carcinoma PANC1 cells. Mice bearing human PANC1 tumor xenografts treated with 3D4S9 had a tumor volume of 84 (±40) mm3 after three weeks, compared with 231 (±150) mm3 in the 3D4scr control group. The 3D4S9 treatment reduced xenograft tumor volume by 60% (A). Mice bearing human PANC 1 tumor xenografts treated with 3D4S9 had a tumor weight of 0.13 (±0.02) g after three weeks, compared with 0.66 (+0.3) g in the 3D4scr control group. The 3D4S9 treatment reduced xenograft tumor weight by 80% (B). The mice were weighed prior to sacrifice. Mice bearing human PANC 1 tumor xenografts treated with the 3D4scr or 3D4S9 had almost the same body weight (C).

We claim:

1. A fusion protein, comprising:

(a) an antibody or an antigen binding fragment thereof (Ab) that specifically binds to DSG2, wherein the antibody comprises a heavy chain having the amino acid sequence of SEQ ID NO: 24 and a light chain sequence having the amino acid sequence of SEQ ID NO: 11; and (b) one or more cell penetrating effector peptide (CPEP) fused to the terminus of the Ab of (a) or fused inside of the Ab of (a), wherein one CPEP comprises: an optional polyanionic domain (PAD), one or two cleavable linkers (CLs), a polycation domain (PCD) and an effector peptide (EP) in an arrangement of (CL-PCD-EP), (CL-EP-PCD), (PAD-CL-PCD-EP), (CL-EP -PCD-CL-PAD), EP-PCD-CL), (PCD-EP-CL), (EP-PCD-CL-PAD) or (PAD-CL -PCD-EP-CL) from N-terminus to C-terminus, when the CPEP is fused to the terminus of the Ab of (a), or one CPEP comprises: an optional polyanionic domain (PAD), two cleavable linkers (CLs), a polycation domain (PCD) and an effector peptide (EP) in an arrangement of (CL-PCD-EP-CL), (CL-EP-PCD-CL), (PAD-CL-PCD-EP-CL), (PAD-CL-EP -PCD-CL), (CL-EP-PCD-CL-PAD) or (CL-PCD-EP-CL-PAD), from N-terminus to C-terminus, when the CPEP is fused inside of the Ab with its two terminuses;

wherein the PAD of the CPEP is a polyanionic peptide with a sequence comprising 4 to 20 acidic amino acids;

wherein each CL sequence comprises one or more of KPLGLAR (SEQ ID NO: 5), PLGLAG (SEQ ID NO: 6), or KPLGLAG (SEQ ID NO: 7) or a combination thereof, wherein the CL is cleavable in the intracellular environment;

wherein the PCD comprises from 5 to 20 consecutive basic amino acids; and the EP comprises KLAKLAKKLAKLAK (SEQ ID NO: 2), KHSSGCAFL (SEQ ID NO: 3), or KHSPACAFL (SEQ ID NO: 4).

2. The fusion protein of claim 1, wherein the CPEP is fused to the terminus or inside of the heavy chain of the Ab.

3. The fusion protein of claim 1, wherein the antigen-binding fragment of an antibody is a Fab fragment, a Fab' fragment, a Fd fragment, a Fd' fragment, a Fv fragment, a dAb fragment, a F(ab')2 fragment, a single chain fragment, a diabody, or a linear antibody.

4. The fusion protein of claim 1, wherein when the CPEP is fused to the terminus of the Ab of (a), the fusion protein has an arrangement of: (EP-PCD-CL)-Ab, (PCD -EP-CL)-Ab, (EP-PCD-CL-PAD)-Ab, (PAD-CL-PCD-EP-CL)-Ab, Ab-(CL-PCD-EP), Ab-(CL -EP-PCD), Ab-(PAD-CL-PCD-EP) or Ab-(CL-EP-PCD-CL-PAD), from N-terminus to C-terminus.

5. The fusion protein of claim 1, wherein when the CPEP is fused inside of the Ab with its two terminuses, the fusion protein has an arrangement of: $Ab^N$-(CL-PCD-EP -CL)-$Ab^C$, $Ab^N$-(CL-EP-PCD-CL)-$Ab^C$, $Ab^N$-(PAD-CL-PCD-EP-CL)-$Ab^C$, $Ab^N$-(PAD-CL-EP -PCD-CL)-$Ab^C$, $Ab^N$-(CL-EP-PCD-CL-PAD)-$Ab^C$ or $Ab^N$-(CL-PCD-EP-CL-PAD)-$Ab^C$, from N-terminus to C-terminus, wherein $Ab^N$ is the N-terminal fragment of the Ab and $Ab^C$ is the C-terminal fragment of the Ab.

6. The fusion protein of claim 1, wherein the PCD comprises from 5 to 20 consecutive basic amino acids.

7. The fusion protein of claim 1, wherein the PCD comprises from 7 to 12 consecutive basic amino acids.

8. The fusion protein of claim 1, wherein the PCD is selected from the group consisting of polylysine, polyarginine, and polyhistidine, or mixtures thereof.

9. The fusion protein of claim 1, wherein the PCD composition is composed of 8 to 10 consecutive lysine and arginine.

10. The fusion protein of claim 1, wherein the PAD of the CPEP is a polyanionic peptide with a sequence comprising 4 to 20 acidic amino acids.

11. The fusion protein of claim 1, wherein the PAD comprises from 5 to 9 consecutive acidic amino acids.

12. The fusion protein of claim 11, wherein the acidic amino acid is aspartic acid, glutamic acid, phosphoserine, and phosphothreonine.

13. The fusion protein of claim 11, wherein the PAD is 6 to 8 consecutive aspartic acids and glutamic acids.

14. An antibody or an antigen binding fragment thereof that specifically binds to DSG2, and is selected from the group consisting of
- 3D4: a heavy chain having the amino acid sequence of SEQ ID NO: 24 and a light chain sequence having the amino acid sequence of SEQ ID NO: 11;
- 3D4KLA: a heavy chain having the amino acid sequence of SEQ ID NO: 9 and a light chain sequence having the amino acid sequence of SEQ ID NO: 11;
- 3D4S9: a heavy chain having the amino acid sequence of SEQ ID NO: 13 and a light chain sequence having the amino acid sequence of SEQ ID NO: 11;
- 3D4rS9: a heavy chain having the amino acid sequence of SEQ ID NO: 15 and a light chain sequence having the amino acid sequence of SEQ ID NO: 11;
- 3D4rS9-AD6: a heavy chain having the amino acid sequence of SEQ ID NO: 17 and a light chain sequence having the amino acid sequence of SEQ ID NO: 11;
- 3D4rS9-A: a heavy chain having the amino acid sequence of SEQ ID NO: 19 and a light chain sequence having the amino acid sequence of SEQ ID NO: 11;
- 3D4rS9-D: a heavy chain having the amino acid sequence of SEQ ID NO: 21 and a light chain sequence having the amino acid sequence of SEQ ID NO: 11; and
- 3D4Fc-rS9: a heavy chain having the amino acid sequence of SEQ ID NO: 23 and a light chain sequence having the amino acid sequence of SEQ ID NO: 11.

* * * * *